United States Patent
Sivathanu et al.

(10) Patent No.: US 11,813,262 B2
(45) Date of Patent: Nov. 14, 2023

(54) COMPOSITIONS AND METHODS TO INCREASE MUSCULAR STRENGTH

(71) Applicant: Massachusetts Institute of Technology, Cambridge, MA (US)

(72) Inventors: Vivek Sivathanu, Cambridge, MA (US); Roger Dale Kamm, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 584 days.

(21) Appl. No.: 16/761,100

(22) PCT Filed: Nov. 2, 2018

(86) PCT No.: PCT/US2018/059087
§ 371 (c)(1),
(2) Date: May 1, 2020

(87) PCT Pub. No.: WO2019/090171
PCT Pub. Date: May 9, 2019

(65) Prior Publication Data
US 2020/0352940 A1 Nov. 12, 2020

Related U.S. Application Data

(60) Provisional application No. 62/581,690, filed on Nov. 4, 2017.

(51) Int. Cl.
*A61P 21/06* (2006.01)
*A61K 31/506* (2006.01)
*A61K 31/496* (2006.01)

(52) U.S. Cl.
CPC .......... *A61K 31/506* (2013.01); *A61K 31/496* (2013.01); *A61P 21/06* (2018.01)

(58) Field of Classification Search
CPC ...................................................... A61P 27/00
See application file for complete search history.

(56) References Cited

U.S. PATENT DOCUMENTS

| | | | |
|---|---|---|---|
| 2006/0167106 A1* | 7/2006 | Zhang | A61K 31/16 564/76 |
| 2010/0323991 A1 | 12/2010 | Bar-Or | |
| 2010/0324005 A1 | 12/2010 | Bar-Or | |

FOREIGN PATENT DOCUMENTS

WO 2006062732 A2 6/2006

OTHER PUBLICATIONS

Steven S. An et al: "Stiffness changes in cultured airway smooth muscle cells", American Journal of Physiology. Cell Physiology. ,vol. 283, No. 3, Sep. 1, 2002 (Sep. 1, 2002), pp. C792-C801, XP055544789, US ISSN: 0363-6143, DOI:10.1152/ajpce11.00425. 2001, abstract p. C800, col. 2, last paragraph.
Johan Lindquist et al: "Modulating myosin restores muscle function in a mouse model of nemaline myopathy : Therapy for Nemaline Myopathy", Annals of Neurology., vol. 79, No. 5, May 1, 2016 (May 1, 2016), pp. 717-725, XP055544517, Boston, US ISSN:0364-5134, DOI:10.1002/ana.24619, abstract.
Tadamoto Isogai et al: "SMIFH2 has effects on Formins and p53 that perturb the cell cytoskeleton", Scientific Reports, vol. 5, No. 1, Apr. 30, 2015 (Apr. 30, 2015), XP055544778, DOI: 10.1038/srep09802 abstract Discussion.
Written Opinion of the International Searching Authority for International Patent Application No. PCT/US2018/059087 dated Jan. 28, 2019 (8 pages).
International Search Report for International Patent Application No. PCT/US2018/059087 dated Jan. 28, 2019 (5 pages).

* cited by examiner

*Primary Examiner* — Theodore R. Howell
(74) *Attorney, Agent, or Firm* — PABST PATENT GROUP LLP

(57) ABSTRACT

Provided herein are methods and compositions for increasing muscle strength, and for treating muscle wasting disorders, muscle degenerative disease, or exercise-induced weakness, and cancer.

21 Claims, 23 Drawing Sheets

Specification includes a Sequence Listing.

Securing the muscle
on cantilevers

Electrical stimulation
setup

Electrical stimulation of
mouse muscle explant

Mature sarcomeric myotubes

Immature sarcomeric myotubes

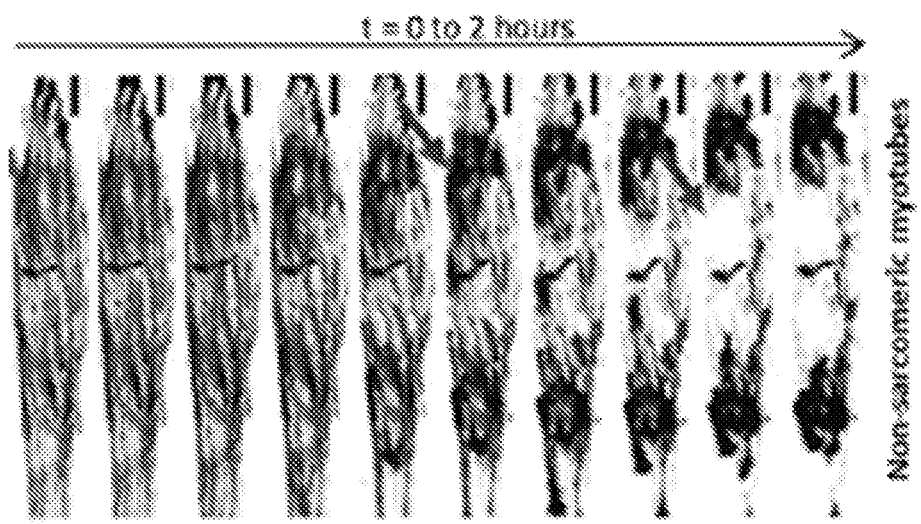
FIG. 10C
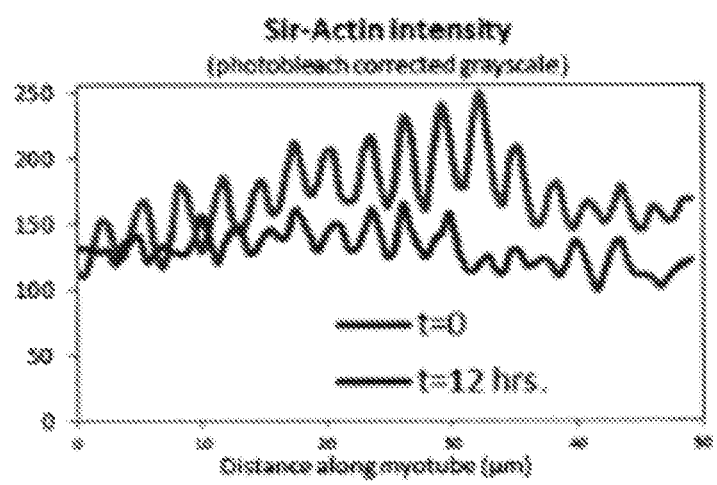
FIG. 10D
FIG. 10E

COMPOSITIONS AND METHODS TO INCREASE MUSCULAR STRENGTH

RELATED APPLICATIONS

This application is a U.S. national stage application filed under 35 U.S.C. § 371 of International Patent Application No. PCT/US2018/059087, filed Nov. 2, 2018, which claims benefit of priority to U.S. Provisional Application No. 62/581,690, filed Nov. 4, 2017, the entire contents of which is incorporated herein by reference.

REFERENCE TO SEQUENCE LISTING

The Sequence Listing submitted Jun. 16, 2023, as a text file named "MIT_19768_371_ST25.txt", created on Jun. 16, 2023, and having a size of 6,425 bytes is hereby incorporated by reference pursuant to 37 C.F.R. § 1.825(b)(2)(i).

STATEMENT UNDER FEDERALLY SPONSORED RESEARCH AND DEVELOPMENT

This invention was made with government support under grant number 0939511 awarded by the National Science Foundation and Technology Center Emergent Behaviors of Integrated Cellular Systems (EBICS). The government has certain rights in the invention.

FIELD OF THE INVENTION

The invention disclosed herein generally relates to compositions and methods for increasing muscle strength.

BACKGROUND OF THE INVENTION

Millions of patients with cancer suffer from skeletal muscle wasting disorders, such as sarcopenia and cachexia, which affect their daily mobility. Additionally, tens of millions of aging patients all over the world are bed-ridden in hospitals or at home during prolonged periods of time during which they too suffer from muscle wasting, thereby affecting their day-to-day mobility and basic functions. In these patients, skeletal muscle cells tend to build up internal resistance when not used frequently, thereby limiting the amount of force they can exert. This makes people have limited mobility, e.g., bed-ridden patients who cannot walk as well, injured body-builders or athletes who cannot perform/lift weights as well as before the injury. These conditions can lead to muscle atrophy. Existing methods for treatment and increasing muscle force include tedious resistance exercise and can often take a substantial amount of time to observe improvement.

Accordingly, compositions and methods are need to increase muscle strength.

SUMMARY OF THE INVENTION

The invention features methods and compositions for increasing muscle strength. For example, muscle strength is increased in the absence of exercise. The methods and compositions provide a solution to a longstanding medical problem of how to treat muscle fatigue and weakness. The invention provides methods of increasing muscle strength in subjects that are not able to exercise, e.g., infirm, physically handicapped, and/or elderly subjects. The methods and compositions are also useful to increase muscle strength in healthy able-bodied individuals, e.g., for muscle recovery after particularly long or strenuous workouts or competition. In some embodiments, the muscle is skeletal muscle. For example, the subject has not been diagnosed with a muscle tissue disorder of a smooth or skeletal muscle disorder. In other examples, the subject has been diagnosed with or is suffering from a clinical smooth or skeletal muscle disorder.

Thus, provided herein are methods and compositions for treatment of wasting disorders, muscle weakness/degeneration associated with cancer, patients with limited mobility, and athletes. Conditions or pathologies to be treated include Amyotrophic Lateral Sclerosis (ALS) and Duchenne Muscular Dystrophy (DMD). In embodiments, the methods and compositions allow for improved efficiency of skeletal muscle by targeting the dynamic F-actin cytoskeleton.

Subjects to be treated include those diagnosed with or having a muscle wasting disorder, heart disease, exercise-induced muscle weakness, or cancer. In aspects, applications may include diseases or conditions wherein improvement in skeletal muscle strength may be beneficial. In certain aspects, diseases or conditions may include muscle wasting due to AIDS, age-related Sarcopenia, cancer cachexia, Cushing's syndrome, diabetes mellitus and sepsis. Additionally, muscle strength improvement in patients suffering from Amytrophic Lateral Sclerosis (ALS) and Duchenne Muscular Dystrophy (DMD) is described. In further aspects, methods provided herein can be used in healthy patients, for example to improve or increase the level physical exertion the subject can achieve, e.g., increasing their walk or run speed or increase weight that a subject can bear or lift.

For example, a method for increasing muscle strength is carried out by contacting a skeletal or smooth muscle of a subject with a pharmacological agent or a therapeutic agent that reduces mechanical stiffness of a muscle tissue. Mechanical stiffness of a muscle tissue is evaluated using a number of indices, including palpation, quantification of Young's modulus, as well as use of a myotonometer. An exemplary pharmacological agent is an F-actin disrupting agent which depolymerizes actin. For example, actin in muscle tissue is transiently or temporarily depolymerized. Exemplary pharmacological agents include SMIFH2 or ATM-3507. Other pharmacological agents to be used in the methods include microtubule disrupting agent, e.g., paclitaxel, or an intermediate filament disrupting agent.

The F-actin disrupting agent, microtubule disrupting agent and/or intermediate disrupting agent are administered alone or in combination. If more than one class of agent is administered, the agents can be administered simultaneously, e.g., as a mixture, or sequentially, e.g., in a combination therapy approach.

In some situations, the skeletal or smooth muscle is diseased or functionally compromised. Alternatively, the skeletal or smooth muscle is normal, healthy tissue, which is sought to be augmented or strengthened. The methods are useful to treat a subject that comprises a muscle wasting disorder, a muscle degenerative disease, or exercise-induced muscle weakness. The agents are administered such the muscle tissue is directly or indirectly contacted. The methods lead to an increase in muscle strength, e.g., muscle strength is increased by at least 10% (20%, 50%, 75%, 2-fold, 5-fold, 10-fold or more) compared to the level of muscle strength prior to the contacting the muscle with the agent. Increase in muscle strength commences 0.1-5, e.g., 0.2, 0.5, 1, 2, 3, or 4, hours post-administration of the agent.

The agent comprises a small molecule or a polypeptide. A small molecule is a compound that is less than 2000 daltons in mass. The molecular mass of the small molecule is preferably less than 1000 daltons, more preferably less than 600 daltons, e.g., the compound is less than 500 daltons, 400 daltons, 300 daltons, 200 daltons, or 100 daltons.

Also within the invention is a composition comprising a unit dose of an F-actin disrupting agent in an amount to depolymerize F-actin, disrupt microtubules, or disrupt intermediate filaments in mammalian skeletal or smooth muscle. The composition optionally pharmaceutically-acceptable excipient. The excipient is inactive, e.g., does not have an activity of the pharmacological agent, i.e., to depolymerize F-actin, disrupt microtubules, or disrupt intermediate filaments in mammalian skeletal or smooth muscle An exemplary method for increasing muscle strength in a subject is carried out by contacting a skeletal muscle of the subject with an F-actin disrupting agent and transiently depolymerizing actin. For example, the skeletal muscle is diseased or functionally compromised, e.g., diseased or functionally compromised skeletal muscle is the result of a muscle wasting disorder, cancer, or exercise-induced muscle weakness. Examples of muscle wasting disorders include Amyotrophic Lateral Sclerosis (ALS), Duchenne Muscular Dystrophy (DMD), cachexia, sarcopenia, human immunodeficiency syndrome (HIV), diabetes mellitus, or sepsis. Alternatively, the skeletal muscle is healthy skeletal muscle. The subject to be treated is preferably a mammalian subject. As is described above, muscle strength is increased by at least 10% compared to the level of muscle strength prior to the contacting step, and an increase in muscle strength commences about 0.1-5 hours post-administration of the agent. In some treated individuals, an increase in muscle strength commences about 24 hours post-administration of the agent. Exemplary agents include a small molecule, a peptide, or a nucleic acid molecule. Such agents may comprise actin barbed-end binders, G-actin sequestering agents, actin nuclease inhibitors, tropomyosin inhibitors, actin pointed end modifiers, actin severing agents, actin capping modifiers, or upstream modifiers, or any combination thereof.

Also within the invention is a composition comprising a unit dose of an F-actin disrupting agent in an amount to transiently depolymerize F-actin in mammalian skeletal muscle, and a pharmaceutically-acceptable excipient as well as a composition comprising a unit dose of an F-actin disrupting agent in an amount to continuously depolymerize F-actin in mammalian skeletal muscle, and a pharmaceutically-acceptable excipient.

Another exemplary method of treating a subject who has a muscle wasting disorder, cancer, or exercise-induced muscle weakness is carried out by administering a pharmaceutical composition comprising an F-actin disrupting agent to the subject, e.g., a mammal. Examples of types of agents to be administered include a small molecule, a peptide, or a nucleic acid molecule. Muscle wasting disorder include ALS, DMD, cachexia, sarcopenia, human immunodeficiency syndrome (HIV), diabetes mellitus, or sepsis.

The subject to be treated include mammals. In an embodiment, the mammal is a human. In other embodiments, the mammal is a non-human, including, but not limited to horses, dogs and cats.

The invention described herein provides advantages over existing methods of increasing muscle force (i.e., strength) that involve tedious resistance exercise and typically take days to weeks to see an improvement in external force. In particular, the disclosure herein, provides for methods that take effect immediately (for example, within hours of administration).

Each of the aspects and embodiments described herein are capable of being used together, unless excluded either explicitly or clearly from the context of the embodiment or aspect. All references cited herein are incorporated by reference.

BRIEF DESCRIPTION OF THE DRAWINGS

FIG. 8F is a graph showing that ZygoA treatment of the 3D muscle tissues leas to a significant improvement in contraction relative to DMSO treated controls, reaching ~2-fold increase in 2 hours.

FIG. 10C is an image depicting that poorly differentiated, myotubes without visible sarcomeric structures had rupturing F-actin cables and significant actin upon actin disruption with ZygoA. FIG. 10D is a graph showing the Sir-Actin intensity before and 12 hours after treatment along sarcomeric F-actin in mature myotubes. FIG. 10E is a graph quantification which showed a decrease in the average F-actin filament length as well as an increase in number of F-actin filaments as shown in (FIG. 10E).

DETAILED DESCRIPTION OF THE INVENTION

Figure 1A:
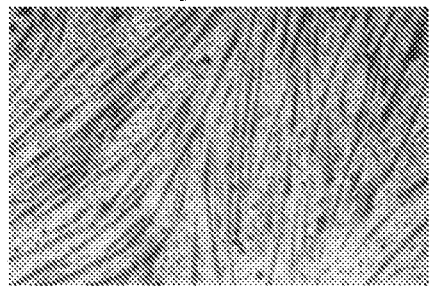
FIG. 1A is an image of mouse muscle myoblast C2Cl2 cells.
Figure 1B:
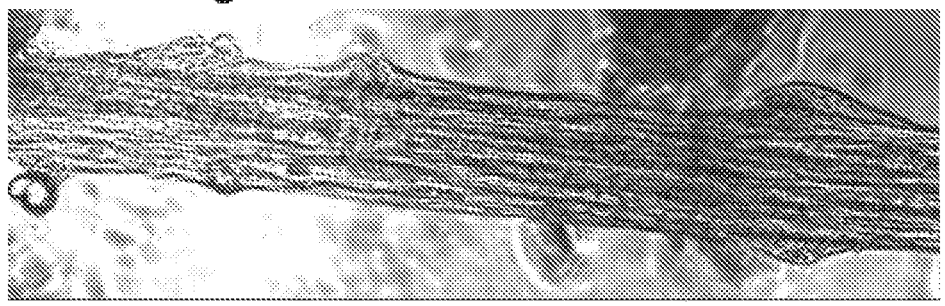
FIG. 1B is an image of engineered skeletal muscle tissue.
Figure 1C:
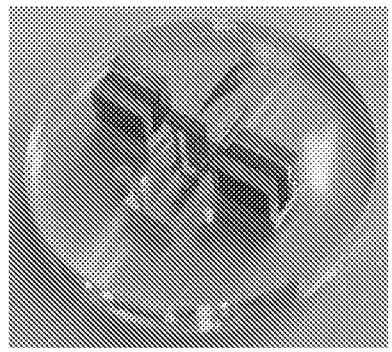
FIG. 1C is an image showing a custom contractility tester.
Figure 1D:
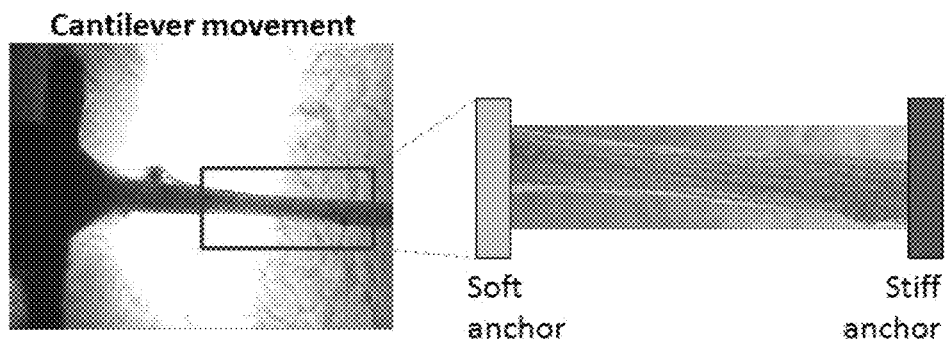
FIG. 1D is an image showing the cantilever movement.
Figure 1E:
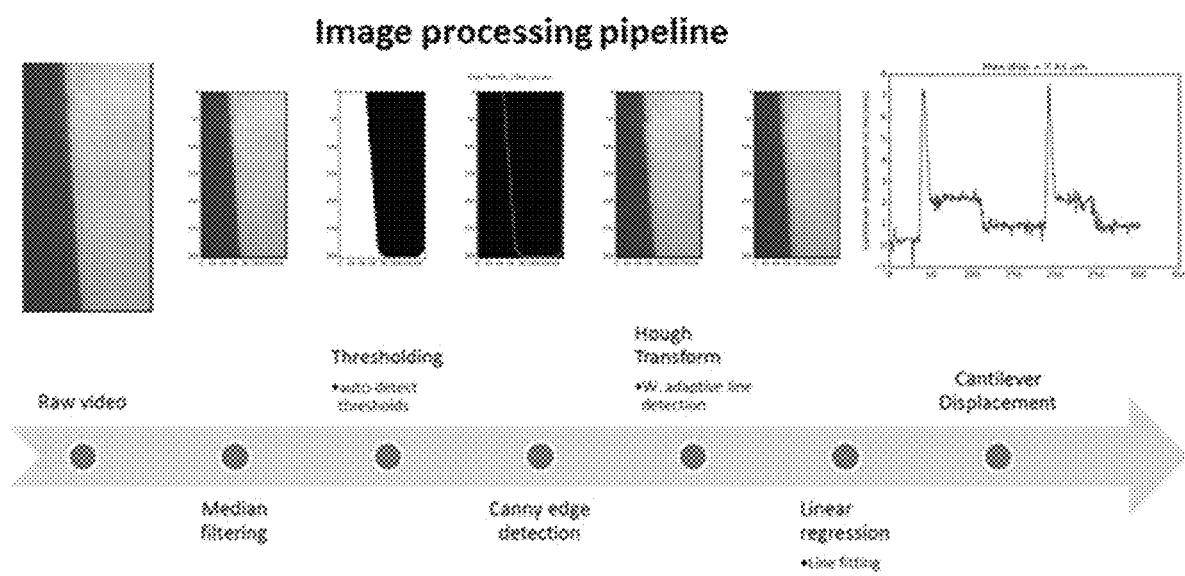
FIG. 1E is a schematic showing the image processing pipeline. A differentiated skeletal muscle tissue and contractility assay is shown.

The present disclosure relates to methods and compositions for increasing muscular strength (e.g., without exercise). More particularly, the present disclosure relates to methods that amplify muscle force by transiently fluidizing the actin cytoskeletal network within muscle cells. The disclosure is based, at least in part, on the unexpected discovery that the active contractility can be amplified by eliciting a transient breakdown and rebuilding of the structural cytoskeletal network within the cells by contacting muscle tissue with a pharmacologic agent. The rebuilt cytoskeletal network elicits over a 2-fold increase in the force produced by the muscle tissue. The increase in force parallels muscle strength. As described herein, any cytoskeletal modifiers (e.g., in particular families include lygosporins, latrunculins, and formin mediated actin assembly inhibitors) elicit the effect.

Muscle regeneration is the process by which damaged (alternatively, functionally compromised or diseased) skeletal, smooth or cardiac muscle undergoes biological repair and forms new muscle in response to death (necrosis) of muscle cells. Cellular events required for regeneration include inflammation, revascularisation and innervation, in addition to myogenesis where new muscle is formed.

Various phases of muscle regeneration take place throughout healing:
1. Degeneration and inflammation phase. This typically occurs within the first few days after trauma. Portions of muscle fibers die and an inflammatory reaction occurs. The necrotic area becomes infiltrated by mononuclear cells, activated macrophages and T-cells. The activated lymphocytes secrete a large number of various messenger substances which subsequently trigger an inflammatory response. The regeneration process is then initiated, but is initially inhibited by the formation of an intra- and extra-muscular haematoma. In addition, the haematoma also promotes the formation of unwanted scar tissue.
2. Reparation phase. In the following 7-10 days the necrotic muscle fiber portions are cleared away by macrophages and regeneration of the muscle begins. The satellite cells migrate into the damaged muscle fibers or form into new fibers. Capillaries also immigrate into the regenerating area. The regeneration process reaches its most active point at approximately 14 days after trauma.
3. Restoration phase (fibrosis). This phase occurs in cross-over with the previous phase and can last as long as four weeks. A normal fiber diameter and the complete differentiation of fiber types is achieved through a re-innervation of the regenerating tissue.

Definitions

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Unless defined otherwise herein, all technical and scientific terms used herein have the same meaning as commonly understood by one of ordinary skill in the art to which this invention pertains.

The term "subject" as used herein is interchangeable with individual or patient, and may refer to a subject to be treated, evaluated or assessed (e.g., diagnosed) using a method, composition, or system provided herein. In some embodiments, the subject is a mammal. In other embodiments, the mammal is a human. In some cases, the methods of the invention find use in experimental animals, in veterinary application, and in the development of animal models for disease, including, but not limited to, rodents including mice, rats, and hamsters, and primates. In embodiments, a subject or "subject in need thereof" is a living member of the animal kingdom suffering from or that may suffer from the indicated disorder. In embodiments, the subject is a member of a species comprising individuals who naturally suffer from the disease. In embodiments, the subject is a mammal. Non-limiting examples of mammals include rodents (e.g., mice and rats), primates (e.g., lemurs, bushbabies, monkeys, apes, and humans), rabbits, dogs (e.g., companion dogs, service dogs, or work dogs such as police dogs, military dogs, race dogs, or show dogs), horses (such as race horses and work horses), cats (e.g., domesticated cats), livestock (such as pigs, bovines, donkeys, mules, bison, goats, camels, and sheep), and deer. In embodiments, the subject is a human. In embodiments, the subject is a non-mammalian animal such as a turkey, a duck, or a chicken. In embodiments, a subject is a living organism suffering from or prone to a disease or condition that can be treated by administration of a composition or pharmaceutical composition as provided herein. In other embodiments, the subject is a non-human mammal, e.g., including horses, dogs and cats.

"Treatment," "treat," or "treating." as used herein covers any treatment of a disease or condition of an individual and includes, without limitation: (a) preventing the disease or condition from occurring in an individual which may be predisposed to the disease or condition but has not yet been diagnosed as having it; (b) inhibiting the disease or condition, e.g., arresting its development; (c) relieving and or ameliorating the disease or condition, e.g., causing regression of the disease or condition; or (d) curing the disease or condition, e.g., stopping its development or progression. In embodiments, the population of individuals treated by the methods of provided herein includes individuals suffering from the undesirable condition or disease, as well as individuals at risk for development of the condition or disease. In embodiments, "treating" is in reference to a subject with a muscle wasting disorder, heart disease, exercise-induced muscle weakness, or cancer.

As used herein, "therapeutically effective amount" refers to an amount which is effective in reducing, eliminating, treating, preventing or controlling a symptom (e.g., one or more symptoms) of a disease or condition (such as, a waste disorder, a cardiovascular disease, or cancer). The term "controlling" is intended to refer to all processes wherein there may be a slowing, interrupting, arresting, or stopping of the progression of a diseases and condition, but does not necessarily indicate a total elimination of all disease and condition symptoms, and is intended to include prophylactic treatment.

In embodiments, the therapeutically effective amount is the quantity of the agent which can promote muscle strength. Alternatively, an "effective amount" is the quantity of agent which can prevent, slow, arrest or reverse the loss of muscle mass and strength, e.g., resulting from wasting syndromes.

In embodiments, an effective amount of the compound can range from about 0.01 mg/kg to about 20 mg/kg of the active compound of this invention. Preferred daily doses will be about 0.2 to about 10 mg/kg, more preferably about 0.3 to about 5 mg/kg. The amount of compound administered to the subject will depend on the type and severity of the disease or condition and on the characteristics of the individual, such as general health, age, sex, body weight and tolerance to drugs. It will also depend on the degree, severity and type of disease or condition. The skilled artisan will be able to determine appropriate dosages depending on these and other factors.

As used herein, a "wasting syndrome" is a disease or condition which results in, is characterized by or accompanied by a loss of muscle mass and/or strength. Examples of such diseases include AIDS; cancer; demyelinating disorders resulting in muscle atrophy (e.g., multiple sclerosis, amyotropic lateral sclerosis, congenital metabolic disorders such as phenylketonuria. Tay-Sachs disease, Hurler's syndrome and leukodystrophies, postinfections encephalomyelitis, viral encephalitis, aseptic meningitis and HTLV-associated myelopathy); dystrophic disease (e.g., muscular dystrophy, Duchenne dystrophy, Landouzy-Dejerine muscular dystrophy, and limb-girdle muscular dystrophy); generalized and focal dystonia; eating disorders (e.g., anorexia and bulimia); cachexia or wasting due to chronic diseases; and vascular disorders (e.g., infarction). Loss of muscle mass and/or strength can also occur in subjects undergoing certain types of chemotherapy, or as a consequence of aging, malnutrition, or muscle deconditioning. Muscle deconditioning commonly occurs in individuals who experience a prolonged period in a weightless environment such as outer space, are bedridden for extended period of time, or have certain muscles or muscle groups immobilized, such as in a cast. Such individuals comprise normal healthy muscle tissue, and a clinical benefit is achieved using the methods described herein. Individuals requiring prolonged bedrest include those with chronic diseases and those suffering from temporary paralysis from spinal cord injuries resulting from, for example, hematoma or compression; such individuals also comprise normal healthy muscle tissue, and a clinical benefit is achieved using the methods described herein. In some embodiments, the clinical wasting disorder to be treated is cachexia.

"Cachexia" is weakness and a loss of weight caused by a disease or as a side effect of illness. Cardiac cachexia, i.e. a muscle protein wasting of both the cardiac and skeletal muscle, is a characteristic of congestive heart failure. Cancer cachexia is a syndrome that occurs in patients with solid tumors and hematological malignancies and is manifested by weight loss with massive depletion of both adipose tissue and lean muscle mass. Acquired Immunodeficiency Syndrome (AIDS). Cachexia is a Human Immunodeficiency Virus (HIV) associated myopathy and/or muscle weakness/wasting that is a relatively common clinical manifestation of AIDS. Individuals with HIV-associated myopathy or muscle weakness or wasting typically experience significant weight loss, generalized or proximal muscle weakness, tenderness, and muscle atrophy.

In embodiments, the muscle disorder is "sarcopenia." Sarcopenia is a debilitating disease that afflicts the elderly and chronically ill patients and is characterized by loss of muscle mass and function. It is well established that anabolic steroids can prevent and/or reverse losses in lean body mass (decrease in skeletal muscle mass) associated with age, disease and trauma injury. Further, increased lean body mass is associated with decreased morbidity and mortality for certain muscle-wasting disorders.

The terms "muscle wasting" or "muscular wasting", used herein interchangeably, refer to the progressive loss of muscle mass and/or to the progressive weakening and degeneration of muscles, including the skeletal or voluntary muscles which control movement, cardiac muscles which control the heart, and smooth muscles.

Muscular atrophy, as used herein, refers to a partial or complete loss of muscle mass. Muscle dystrophy is a muscle disease involving progressive muscle weakness and atrophy and death of muscle cells and tissues. Muscle atrophy may include diseases or conditions accompanied by, for example, muscle weakness accompanied by muscle atrophy, in particular, a decrease in muscle mass or muscle weakness of proximal muscles, a decrease in muscle function, a decrease of muscle mass, etc. Muscular atrophy or muscle dystrophy may be muscular atrophy caused by long-term bed rest, muscular atrophy caused by an assistive device for therapy, or muscular atrophy caused by cachexia, amyotrophic lateral sclerosis, spinal progressive muscular atrophy, muscular dystrophy, or a combination thereof.

As used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds, e.g., nucleic acid molecules, polynucleotides, polypeptides, proteins, or small molecules are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (RNA or DNA) is free of the genes or sequences that flank it in its naturally-occurring state. Similarly, a purified peptide or protein (e.g., identified by a specific amino acid sequence) is free of the amino acids that flank it in its naturally-occurring state. Purified also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

As used herein, the singular terms "a," "an," and "the" include the plural reference unless the context clearly indicates otherwise.

F-Actin

Actin is a family of globular multi-functional proteins that form microfilaments. It is found in essentially all eukaryotic cells. An actin protein's mass is roughly 42-kDa, with a diameter of 4 to 7 nm, and it is the monomeric subunit of two types of filaments in cells: microfilaments, one of the three major components of the cytoskeleton, and thin filaments, part of the contractile apparatus in muscle cells. It can be present as either a free monomer called g-actin (globular) or as part of a linear polymer microfilament called F-actin (filamentous), both of which are essential for such important cellular functions as the mobility and contraction of cells during cell division.

F-actin has a filamentous structure. The f-actin polymer is considered to have structural polarity due to the fact that all the microfilament's subunits point towards the same end. This gives rise to a naming convention: the end that possesses an actin subunit that has its ATP binding site exposed is called the "(−) end", while the opposite end where the cleft is directed at a different adjacent monomer is called the "(+) end. The terms "pointed" and "barbed" referring to the two ends of the microfilaments derive from their appearance under transmission electron microscopy when samples are examined following a preparation technique called "decoration". Additionally, F-actin polymerization is faster at the barbed end than it is at the pointed end. As a result, the barbed end is also sometimes referred to as the polymerizing end of F-actin.

The helical F-actin filament found in muscles also contains a tropomyosin molecule, which is a 40 nm protein that is wrapped around the F-actin helix. During the resting phase the tropomyosin covers the actin's active sites so that the actin-myosin interaction cannot take place and produce muscular contraction. There are other protein molecules bound to the tropomyosin thread, these are the troponins that have three polymers: troponin I, troponin T and troponin C. F-actin can also be fluidized, wherein polymeric F-actin is converted to g-actin monomers. In examples, this may be referred to as F-actin disruption.

An amino acid sequence for human F-actin is publically available in the GenBank database under accession number NP_001092.1 (SEQ ID NO: 1) and is as follows:

```
  1 mdddiaalvv dngsgmckag fagddaprav fpsivgrprh qgvmvgmgqk dsyvgdeaqs
 61 krgiltikyp iehgivtnwd dmekiwhhtf ynelrvapee hpvllteapl npkanrekmt
121 qimfetfntp amyvaiqavl slyasgrttg ivmdsgdgvt htvpiyegya lphailrldl
181 agrdltdylm kiltergysf tttaereivr dikeklcyva ldfeqemata assssleksy
241 elpdgqviti gnerfrcpea lfqpsflgme scgihettfn simkcdvdir kdlyantvls
301 ggttmypgia drmqkeital apstmkikii apperkysvw iggsilasls tfqqmwiskq
361 eydesgpsiv hrkcf
```

Additional human F-actin sequences are publically available in the GenBank database under accession number and version: NCBI: NP_001128119.1, NP_001606.1, Q6NYC8.1, AAA87395.1, P60709 and BAD96946.1 and are incorporated herein by reference.

A nucleotide sequence that encodes human F-actin is publically available in the GenBank database under accession number and version NM_001101.4 (SEQ ID NO: 2) and is as follows (the start and stop codons are underlined and bolded):

```
   1 gagtgagcgg cgcggggcca atcagcgtgc gccgttccga aagttgcctt ttatggctcg
  61 agcggccgcg gcggcgccct ataaaaccca gcggcgcgac gcgccaccac cgccgagacc
 121 gcgtccgccc cgcgagcaca gagcctcgcc tttgccgatc cgccgcccgt ccacacccgc
 181 cgccagctca ccatggatga tgatatcgcc gcgctcgtcg tcgacaacgg ctccggcatg
 241 tgcaaggccg gcttcgcggg cgacgatgcc ccccgggccg tcttcccctc catcgtgggg
 301 cgccccaggc accagggcgt gatggtgggc atgggtcaga aggattccta tgtgggcgac
 361 gaggcccaga gcaagagagg catcctcacc ctgaagtacc ccatcgagca cggcatcgtc
 421 accaactggg acgacatgga gaaaatctgg caccacacct tctacaatga gctgcgtgtg
 481 gctcccgagg agcacccggt gctgctgacc gaggccccc tgaacccaa ggccaaccgc
 541 gagaagatga cccagatcat gtttgagacc ttcaacaccc cagccatgta cgttgctatc
 601 caggctgtgc tatccctgta cgcctctggc cgtaccactg gcatcgtgat ggactccggt
 661 gacggggtca cccacactgt gcccatctac gagggtatg ccctccccca tgccatcctg
 721 cgtctggacc tggctggccg ggacctgact gactacctca tgaagatcct caccgagcgc
 781 ggctacagct tcaccaccac ggccgagcgg gaaatcgtgc gtgacattaa ggagaagctg
 841 tgctacgtcg ccctggactt cgagcaagag atggccacgg ctgcttccag ctcctccctg
 901 gagaagagct acgagctgcc tgacggccag gtcatcacca ttggcaatga gcggttccgc
 961 tgccctgagg cactcttcca gccttccttc ctgggcatgg agtcctgtgg catccacgaa
1021 actaccttca actccatcat gaagtgtgac gtggacatcc gcaaagacct gtacgccaac
1081 acagtgctgt ctggcggcac caccatgtac cctggcattg ccgacaggat gcagaaggag
```

-continued
```
1141 atcactgccc tggcacccag cacaatgaag atcaagatca ttgctcctcc tgagcgcaag 1201 tactccgtgt ggatcggcgg ctccatcctg gcctcgctgt ccaccttcca gcagatgtgg 1261 atcagcaagc aggagtatga cgagtccggc ccctccatcg tccaccgcaa atgcttctag

1321 gcggactatg acttagttgc gttacaccct ttcttgacaa aacctaactt gcgcagaaaa 1381 caagatgaga ttggcatggc tttatttgtt tttttgttt tgttttggtt tttttttttt 1441 ttttggcttg actcaggatt taaaaactgg aacggtgaag gtgacagcag tcggttggag 1501 cgagcatccc ccaaagttca caatgtggcc gaggactttg attgcacatt gttgtttttt 1561 taatagtcat tccaaatatg agatgcgttg ttacaggaag tcccttgcca tcctaaaagc 1621 caccccactt ctctctaagg agaatggccc agtcctctcc caagtccaca caggggaggt 1681 gatagcattg ctttcgtgta aattatgtaa tgcaaaattt ttttaatctt cgccttaata 1741 ctttttatt ttgttttatt ttgaatgatg agccttcgtg ccccccttc cccttttt 1801 gtcccccaac ttgagatgta tgaaggcttt tggtctccct gggagtgggt ggaggcagcc 1861 agggcttacc tgtacactga cttgagacca gttgaataaa agtgcacacc ttaaaaatga 1921 ggaaaaaaaa aaaaaaaaa
```

Compositions and compounds used in the methods described herein disrupt F-actin to reduce rigidity of the muscle, thereby softening the muscle and leading to an increase in muscle strength. Cytochalasins are fungal metabolites that have the ability to bind to actin filaments and block polymerization and the elongation of actin. Such compounds were used to illustrate the principle of muscle strengthening in mouse model experiments described below. Other F-actin disruptors/inhibitors described herein may be better tolerated and may be used clinically.

Actin exists in both monomeric (G-actin) and polymerized (F-actin) form. Equilibrium between these states is ATP dependent and regulated by a variety of actin-associated proteins. Actin filaments can be either stable, with their lengths precisely specified, or dynamic, undergoing rapid polymer elongation and shrinkage. Stable actin filaments underlie specialized cellular structures, like muscle sarcomeres, brush border microvilli, and hair-cell stereocilia. Dynamic actin filaments mediate various types of cellular motility, including migration, membrane ruffling, and filopodial extension. Events mediated by dynamic actin filaments are arrested rapidly in the presence of actin assembly inhibitors (AAIs) like the cytochalasins and latrunculins). These classes of compounds work by distinct mechanisms to induce net depolymerization of dynamic actin filaments, but they have comparatively little effect on more stable filaments that turn over slowly.

According to the invention, the methods are used to induce transient F-actin disruption. The inhibitors/disruptors are administered in a relatively short pulse, e.g., for a number of hours (e.g., 0.25, 0.5, 0.75, 1.0, 1.25, 1.5, 1.75, 2.0, 3.0, 4.0, 5.0 hours), followed by a recovery period, which then leads to an increase in muscle strength. For example, a relatively high concentration of an F-actin inhibitor/disrupting agent is administered for a short-pulse treatment regimen, e.g. 3 mM cytochalasin for approximately 2 hours to disrupt stable actin. In an alternative treatment regimen, dynamic actin is disrupted using a relatively low concentration of an F-actin disrupting agent using a continuous administration course. e.g., for a number of days, e.g., 1, 1.5, 2.0, 2.5 days. In the latter approach, a lower concentration of the disruptor is used over a longer period of time compared to the method to disrupt stable action, e.g., 0.3 mM cytochalaisin over a period of 2 days.

Multiple pools of actin exist in skeletal muscle tissue. High concentration of disrupting agent for a relatively short period of time leads to disruption of the stable pool of F-actin, whereas a low concentration of the agent for a continuous (long term) disrupts the less stable (dynamic) F-actin. To disrupt dynamic F-actin, the dose may be ¹⁄₁₀ to ¹⁄₁₀₀ of the concentration used to disrupt stable F-actin. The concentration to achieve one or the other effect is determined by dose response analysis, and the ratio (or difference in concentration used) depends on the F-actin disruptor used. In some cases, the continuous/low concentration dose may be better tolerated and safer for certain classes of subjects to be treated.

The mechanism of increasing muscle strength is not specific to a particular disease or even to pathologic state vs. a healthy normal state. The methods are suitable for treatment of disease, e.g., ALS, DMD, as well as augmentation muscle strength in normal, healthy (not diseased) individuals. The route of administration is local, e.g., by injection or topical administration such as a patch, or systemic, e.g., infusion such as intravenous delivery, or orally. For example, tropomyosin inhibitors can be administered systemically, e.g., intravenously, via the bloodstream. In some examples, the inhibitor or disrupting agent is specific for skeletal muscles; in other examples, the inhibitor or disrupting agent is specific for smooth muscle; in yet other examples, the inhibitor or agent affects both classes of muscle tissue. In preferred embodiments, sarcomeric (banded) actin is not affected (or minimally affected). The methods preferably affect background actin, i.e., not banded actin, which may be characterized as stable or dynamic actin. Exemplary turnover time (time to disrupt actin) is, e.g., on the order of minutes (e.g., 1-10 minutes) or on the order of seconds (e.g., 0.1-10, 20, 30, 40, 50 seconds).

The increase in muscle strength is due to (1) disruption of F-actin, and/or (2) reduction of muscle stiffness. Disruption of F-actin is measured by methods known in the art, e.g., examination muscle tissue biopsy samples, live imaging of labeled (e.g., fluorescent) actin, and/or intravital microscopy or atomic force microscopy. Reduction of muscle stiffness (increase in muscle elasticity) is evaluated using known methods such as physical means, e.g., probing with a stiffness probe/gauge, or examination using microscopy such as atomic force microscopy. The methods described herein lower axial stiffness of muscle tissue at the cellular level and at the tissue level. Agents that make muscles more stiff (e.g., agents that increase F-actin polymerization) lead to more rigid muscle tissue and reduced muscle strength.

The present disclosure provides pharmaceutical compositions comprising an amount of a pharmacological agent or a therapeutic agent as described supra. For example, the pharmacological agent or the therapeutic agent may comprise an F-actin disrupting agent. The F-actin disrupting agent may include but is not limited to actin barbed-end binders (e.g., lygosporins), G-actin sequestering agents (e.g., latrunculins, gelsolin, or deacts-GS1), actin nuclease inhibitors (SMIFH2 or CK666), tropomyosin inhibitors (e.g., TR100 or ATM-3507), actin pointed end modifiers (e.g., profiling), actin severing agents (e.g., ADF, cofilin, or gelsolin), agents that modify the ratio of G-actin-ATP to G-Actin-ADP (e.g., Deacts-SpvB), actin capping modifiers (e.g., CapZ modifiers, or tropomodulin), or upstream modifiers (e.g., mDia inhibitors, Rho inhibitors, Rho kinase (ROCK) inhibitors, FAK inhibitors, Talk inhibitors. Vinculin inhibitors, or integrin inhibitors), or any combination thereof. For example, the F-actin disrupting agent is Cytochalasin D (e.g. Zygosporin A). Exemplary ROCK inhibitors include, but are not limited to Fasudil, Ripasudil, RKI-1447, Y-27632, GSK429286A, or, Y-30141. Also, exemplary FAK inhibitors include, but are not limited to: FAK inhibitor 14, PF 431396, PF 573228 or Y11.

An exemplary F-actin disrupting agent comprises an actin nuclease inhibitor, e.g., SMIFH2 (CAS No.: CAS 340316-62-3; 1-(3-Bromophenyl)-5-(2-furylmethylene)-2-thioxo-hexahydropyrimidine-4,6-dione). SMIFH2 derivatives or analogs are also contemplated. SMIFH2 is a small molecule inhibitor of formin-mediated actin assembly that disrupts formin dependent processes from yeast to mammals. The chemical structure of SMIFH2 is provided below:

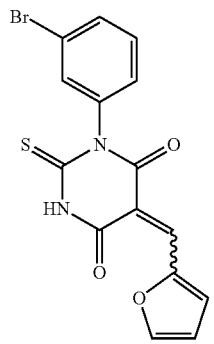 [SMILES: O=C1NC(=S)N(c2cccc(Br)c2)C(=O)C1=Cc1ccco1]

Another exemplary F-actin disrupting agent comprises a tropomyosin inhibitor, e.g., ATM-3507 (CAS No.: 1861449-70-8; (3-((2,3-dimethyl-1-(3-(4-methylpiperazin-1-yl)propyl)-1H-indol-5-yl)oxy)phenyl)(4-(4-fluorophenethyl)piperazin-1-yl)methanone. ATM-3507 derivatives or analogs are also contemplated. ATM-3507 is a tropomyosin inhibitor. The chemical structure of ATM-3507 is provided below:

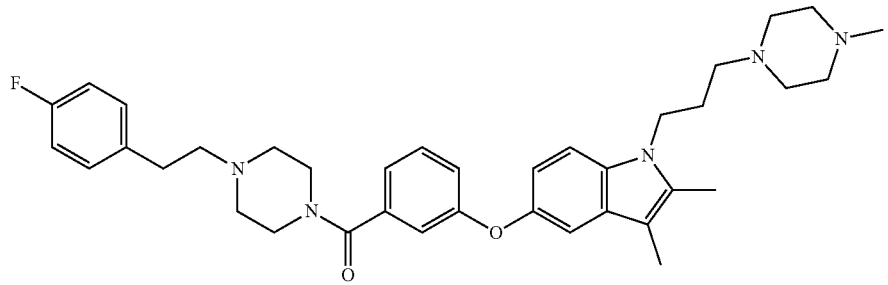 [SMILES: Cc1c(C)n(CCCN2CCN(C)CC2)c2ccc(Oc3cccc(C(=O)N4CCN(CCc5ccc(F)cc5)CC4)c3)cc12]

Microtubule Disrupting Agents

In some examples, the pharmacological agent or the therapeutic agent comprises a microtubule disrupting agent (e.g., a microtubule-binding agent). In dividing cells, microtubules that comprise the mitotic spindle are highly dynamic and sensitive to therapeutic inhibitors. Thus, agents that disrupt (or alter) microtubule function are used to treat patients with cancer. Microtubule disrupting agents (e.g., inhibitors) are a class of compounds that inhibit the function of cellular microtubules. An exemplary microtubule disrupting agent includes paclitaxel (trade name: Taxol). Paclitaxel is a chemotherapy medication used to treat a number of types of cancer, including ovarian cancer, breast cancer, lung cancer, Kaposi sarcoma, cervical cancer, and pancreatic cancer. Additional microtubule disrupting agents include vinflunine, cevipabulin, eribulin, ombrabulin, 2-methoxyoestradiol, indibulin, discodermolide, ixabepilone, cyclostrepin, eleutherobin, laulimalide, noscapine, peloruside, and estramustine. A review by Charles Dumontet and Mary Ann Jordan also provides an overview of microtubule-binding agents (disrupting agents). See Dumontet, C. and Jordan, M. "Microtubule-binding agents: a dynamic field of cancer therapeutics." *Nature Reviews: Drug Discovery.* 9; (2010) 790-803, incorporated herein by reference in its entirety. For example. Table 2 on pages 797-798 of the review article describes a number of microtubule binding agents (e.g., disrupting agents).

Microtubule disrupting agents are also useful to increase muscle strength as described herein. For this purpose, the agents are administered at a dose that is less than the dose used to treat cancer. For example, the dose of a microtubule disrupting agent is 10%, 20%, 30%, 40%, 50%, 2-fold, 5-fold, 10-fold or more, less than the dose administered to treat cancer. For example, the microtubule disrupting agent is administered at a dose of about 0.1-10 mg/mL, e.g., about 1 mg/mL. The amount administered is tailored to the size of the subject and level of muscle function or the individual to be treated.

Intermediate Filament Disrupting Agents

The pharmacological agent or the therapeutic agent may comprise an intermediate filament disrupting agent. Intermediate filaments typically have a diameter of about 10 nm, which is intermediate between the diameters of the two other elements of the cytoskeleton, actin filaments (about 7 nm in diameter) and microtubules (about 25 nm in diameter). In contrast to actin filaments and microtubules, the intermediate filaments are not directly involved in cell movements. Intermediate filaments play a structural role by providing mechanical strength to cells and tissues. See Cooper G M. The Cell: A Molecular Approach. 2nd edition. Sunderland (Mass.): Sinauer Associates; 2000, incorporated herein by reference in its entirety. Intermediate filaments are composed of a variety of proteins that are expressed in different types of cells. For example, in epithelial cells, intermediate filament proteins include acidic keratins and neutral or basic keratins. Additional intermediate filament proteins include vimentin (expressed in fibroblasts, white blood cells, as well as other types of cells), desmin (expressed in muscle cells), glial fibrillary acidic protein (expressed in peripheral neurons), neurofilaments (expressed in neurons), nuclear lamins (expressed in the nuclear lamina of all cell types), and nestin (expressed in stem cells of the central nervous system). Thus, agents that disrupt these intermediate filaments are also contemplated as the pharmacological agents or the therapeutic agents.

Mechanical Stiffness

The pharmacological agent or the therapeutic agent reduces the mechanical stiffness (e.g., increases and/or improves muscle contractility) of the muscle tissue. As described herein, the mechanical stiffness of a muscle or of muscle tissue comprises the empirical evaluation or palpability of the muscle stiffness, rather than the perception or awareness of stiffness by the subject. For example, the mechanical stiffness can be defined by Young's modulus. Young's modulus is a mechanical property that measures the stiffness of a material. It defines the relationship between stress (force per unit area) and strain (proportional deformation) in a material in the linear elasticity regime of a uniaxial deformation. For linear elasticity, a material will undergo elastic deformation when a small load is applied to it in compression or extension. Elastic deformation is reversible (the material returns to its original shape after the load is removed). At near-zero stress and strain, the stress-strain curve is linear, and the relationship between stress and strain is described by Hooke's law that states stress is proportional to strain. The coefficient of proportionality is Young's modulus. The higher the modulus, the more stress is needed to create the same amount of strain; an idealized rigid body would have an infinite Young's modulus.

Figure 2A:
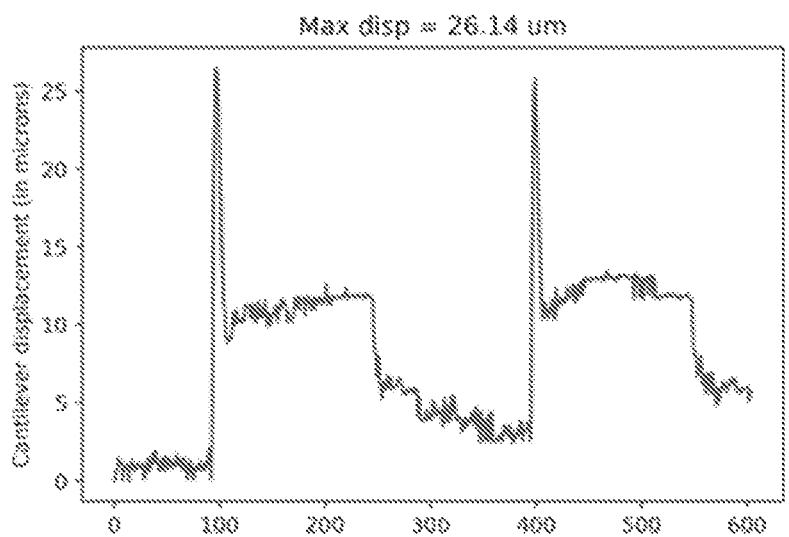
FIG. 2A is a graph showing measured muscle strength pre-treatment.
Figure 2B:
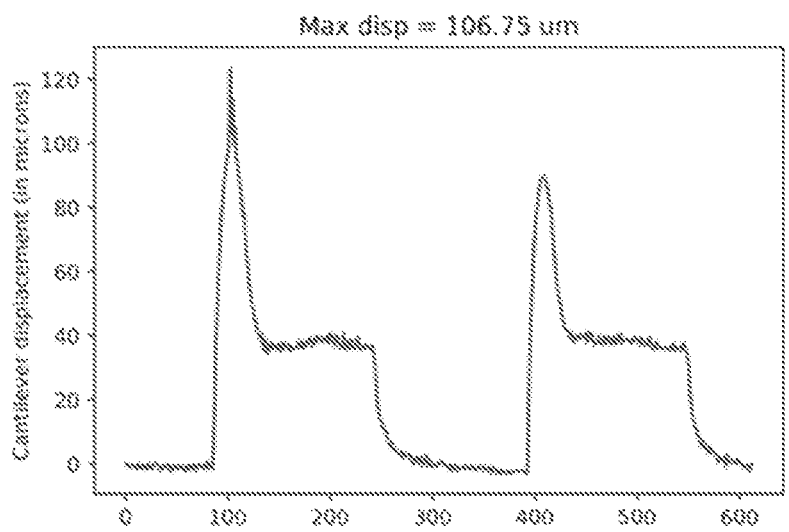
FIG. 2B is a graph showing the measured muscle strength post-treatment, wherein strength becomes approximately 4× within 3 hours. Muscle strength of a sample measured, using the displacement of a compliant anchor is shown.
Figure 3A:
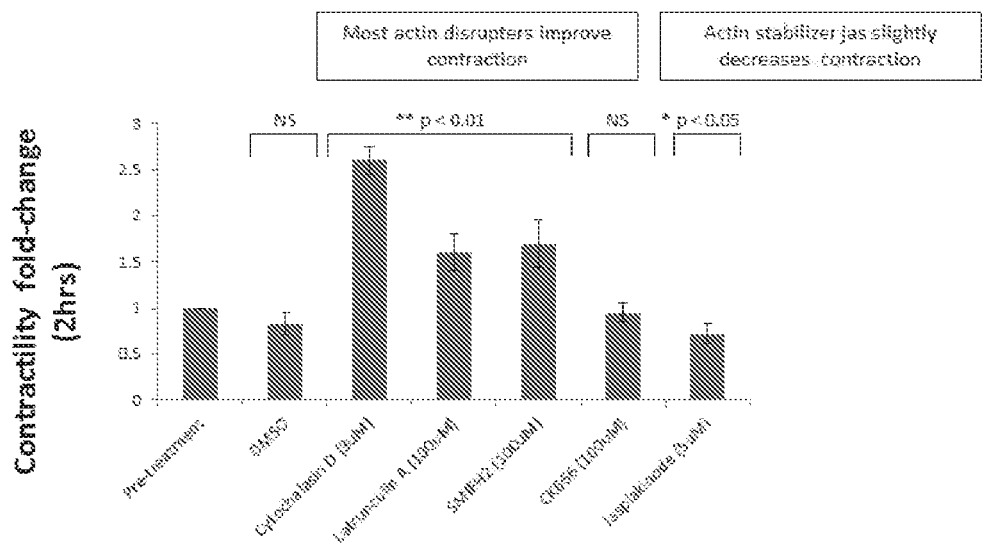
FIG. 3A is a bar graph showing the contractility fold-change of F-actin inhibitors, cytochalasin D (Zygosporin A and cytochalasin D are synonymous).
Figure 3B:
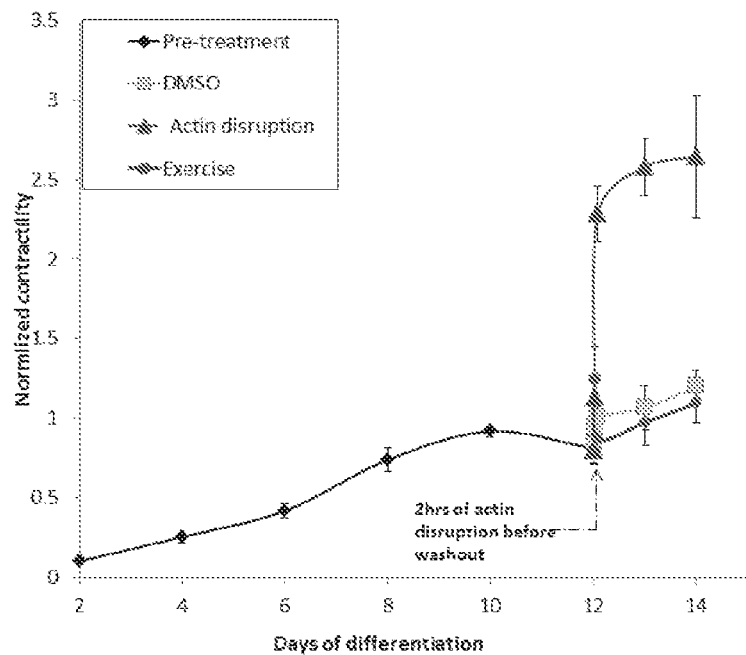
FIG. 3B is a graph showing the normalized contractility versus days of differentiation. A two-hour pulse of cytochalasin D (Zygosporin A and cytochalasin D are synonymous) was used on day 12. Effect of F-actin inhibitors at 2 hours post application is depicted.
Figure 4A:
FIG. 4A is an image showing dissection of extensor digitorum longus (EDL) muscle from a mouse hindlimb.
Figure 4B:
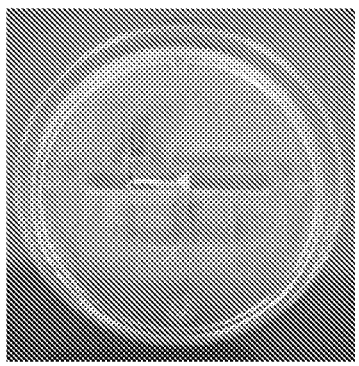
FIG. 4B is an image showing the securing of the EDL muscle from the mouse hindlimb on cantilevers.
Figure 4C:
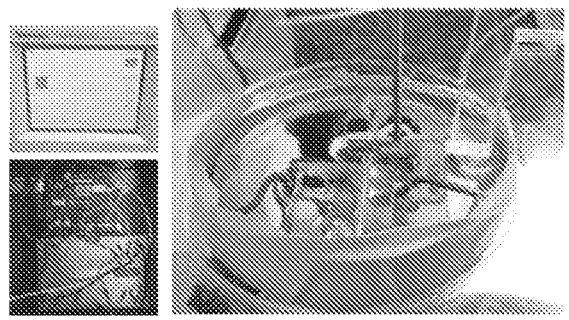
FIG. 4C is an image showing the electrical stimulation set-up.
Figure 4D:
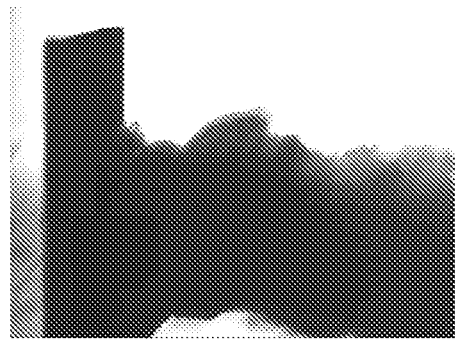
FIG. 4D is an image showing the electrical stimulation of mouse muscle explant. The F-actin disruption showed a persistent increase in force (more than 2-fold) as compared to exercising muscle.

The ranges for Young's modulus in live tissues may be variable. For example, it may depend on the method used to measure or which muscle is being tested. For example, as described by Lima, K, et al, Young's modulus (E) may be defined as the ratio of the longitudinal stress to the longitudinal strain, and represents the tendency of the medium to deform axially when forces opposite and parallel to this axis are applied. See Lima. K. et al., "Assessment of the mechanical properties of the muscle-tendon unit by supersonic shear wave imaging elastography: a review." Ultrasonography, 2018; 37:3-15, incorporated herein by reference in its entirety. Lima, K. et al. describe additional mechanical and acoustic parameters. For example, these include: shear modulus (p), longitudinal stress, longitudinal strain, shear stress, shear strain, viscosity, longitudinal wave, shear wave, acoustic radiation force, shear wave speed ($c_s$), attenuation, isotropic medium, and incompressible medium. Lima, K. et al. describe in FIG. 2, that the gastrocnemius lateralis muscle of a healthy male has a Yong's modulus (E) of about 11.0 t 0.6 kPa (mean i standard deviation). In other examples, the authors studied the mean elasticity (Young's modulus—E) values for muscles and tendons from 127 health volunteers aged 17 to 63. The authors reported that the E values were 11.10±44.10, 10.40±3.70, 31.20±13.00, 74.40±45.70, and 51.50±25.10 kPa for the gastrocnemius and masseter muscles, supraspinatus, and Achilles tendons (longitudinal and transverse planes), respectively. Furthermore, the author's reported that the E of the Achilles tendon was greater in men than in women. Also, they reported that there was no significant correlation between age (up to 63) and E for any structure.

Additionally, in the same paper, the authors reported results of muscle damage in the posterior thigh muscles of 28 rabbits subjected to pressure damage. They reported that E values were collected before the formation of the lesion and 0.5, 2.6, 24, and 72 hours afterwards. The results showed a significant E increase from baseline (6.78±2.06 kPa) to 12.44±3.77 kPa at 0.5 hours, 13.20±3.60 kPa at 2 hours, 10.04±2.95 kPa at 24 hours, and 9.72±3.90 kPa at 72 hours, which corresponded approximately to the recovery level.

Mechanical properties of muscle tissue may also be measured using a handheld myotonometer, e.g., as described in Hu et al., 2018 Scientific Reports, 8, article number 14343, incorporated by reference in its entirety.

As described herein, the Young's modulus reduces after administration of the pharmacological agent or the therapeutic agent. For example, the Young's modulus can reduce by about 1% to about 90%. Alternatively, the Young's modulus can reduce from about 1% to about 80%, from about 1% to about 70%, from about 1% to about 60%, from about 1% to about 50%, from about 1% to about 40%, from about 1% to about 30%, from about 1% to about 20%, from about 1% to about 10%. In other aspects, after administration of the pharmacological agent or the therapeutic agent, the Young's modulus is reduced from about 1% to about 5%, from about 1% to about 4%, from about 1% to about 3%, or from about 1% to about 2%.

In other aspects, after administration of the pharmacological agent or the therapeutic agent, the Young's modulus decreases, relative to a control, (e.g., a healthy subject). For example, "decreased" may refer to any % decrease below a control level. In various embodiments, the decreased level may be at least or about a 5% decrease, at least or about a 10% decrease, at least or about a 15% decrease, at least or about a 20% decrease, at least or about a 25% decrease, at least or about a 30% decrease, at least or about a 35% decrease, at least or about a 40% decrease, at least or about a 45% decrease, at least or about a 50% decrease, at least or about a 55% decrease, at least or about a 60% decrease, at least or about a 65% decrease, at least or about a 70% decrease, at least or about a 75% decrease, at least or about a 80% decrease, at least or about a 85% decrease, at least or about a 90% decrease, at least or about a 95% decrease, relative to a control level.

As used herein, a "control" sample or value may refer to a sample that serves as a reference, usually a known reference, for comparison to a test sample. For example, a control sample or value is one obtained from a normal subject, e.g., a subject characterized by normal/healthy skeletal or smooth muscle/not diseased or functionally compromised (e.g., data or tissue obtained from a healthy individual not diagnosed with a muscle disorder) and compared to an age-matched subject (or subjects) who does have the disease or functionally compromised skeletal or smooth muscle (positive control). Alternatively, a subject in which their skeletal or smooth muscle is not diseased or functionally compromised (e.g., a healthy individual) can be used as a control for individuals wishing to amplify their strength. A control can also represent an average value gathered from a number of tests or results. One of skill in the art will recognize that controls can be designed for assessment of any number of parameters. One of skill in the art will understand which controls are valuable in a given situation and be able to analyze data based on comparisons to control values. Controls are also valuable for determining the significance of data. For example, if values for a given parameter are variable in controls, variation in test samples will not be considered as significant.

Alternatively, after administration of the pharmacological agent or the therapeutic agent, the Young's modulus alters relative to a control, e.g., a healthy subject. As described herein, an "alteration" can also include a 2-fold or more change in the Young's modulus, for example, 5-fold, 10-fold, 20-fold, 30-fold, 40-fold, 50-fold, 100-fold, 500-fold, 1000-fold or more.

The mechanical stiffness of the muscle tissue can also be measured in Pascals, e.g., a unit of pressure used to quantify internal pressure, stress, Young's modulus and ultimate tensile strength. In some examples, the administration of the pharmacological agents or the therapeutic agents described herein can reduce the mechanical stiffness, as evidenced by a decrease in the pressure (Pascals) of the tissue. Janmey, P. and Miller. R. describe the mechanisms of mechanical signaling in development and disease. See Janmey, P. and Miller, R. "Mechanisms of mechanical signaling in development and disease." *Journal of Cell Science* 124, 9-18 (2011), incorporated herein by reference in its entirety. Specifically, the authors describe a number of mechanism that are used to measure cell and tissue mechanics. As described on page 10, these can include, for example:

Stress: the force exerted on an object normalized by the area over which the force is acting.

Tension: the magnitude of a pulling force. Forces in the opposite direction generate compression. For example, activation of myosin within a sarcomere generates tension at cell-cell or cell-tendon junctions.

Strain: a dimensionless number that is the formal definition of deformation; it reports the geometric change in shape of a material under stress. Approximately, it is the distance a material is stretched or compressed relative to its resting length. For examples, cells typically undergo strains of about 10-100% during muscle contraction.

Elasticity: the property of a material to deform to a defined extent in response to a force and then return to its original state when the force is removed.

Elastic modulus, a constant describing the resistance of a material to deformation, defined as the ratio of stress to strain. For example, the elastic modulus for muscle can be in the range from about 104 to about 105 pascals (Pa).

Young's modulus (E): used to quantify elastic resistance to elongation or compression, and the Shear modulus (G) describes the resistance of a material to deformation in shear.

Linear elasticity: a linear relationship between stress and strain; equivalently, the elastic modulus is constant over a range of strains.

Viscosity: the ratio of stress to the rate of strain (or flow rate) for liquids. The viscosity of water, for example, is approximately 1 mPa·s.

Viscoelasticity: the combination of viscosity and elasticity in a material.

Methods of Increasing Muscle Strength

In embodiments, methods provided herein may be used to increase muscle strength. In some examples, the muscle may be skeletal muscle. In other examples, the muscle may be smooth muscle.

In additional embodiments, methods provided herein may be used for the treatment of diseased or functionally compromised skeletal muscle. In embodiments, the subject comprises wasting disorders, heart diseases, or exercise-induced muscle weakness.

In embodiments, the methods provided herein may be used to increase muscle strength in healthy muscle (e.g., to increase walk or run speed or to increase mobility in a subject).

In embodiments, the methods provided herein may be used for the treatment of diseased or functionally compromised skeletal muscle in a subject (e.g., a mammal). In embodiments, the mammal is a human. In other embodiments, the mammal is non-human e.g., including horses, dogs and cats. The methods as used herein may be used for the treatment of horses or dogs, wherein the horses or dogs are involved in racing. In other embodiments, the methods may be used for the treatment of household pets (e.g., dogs or cats) with cancer to increase their mobility.

An effective amount of a therapeutic agent (an F-actin disrupting agent) is administered to the subject in need of treatment. Such subjects are described above. In embodiments, the effective amount is a therapeutically effective amount. In embodiments, the effective amount is the amount effective to increase muscle strength.

In embodiments, the F-actin disrupting agent, the microtubule disrupting agent and/or the intermediate filament disrupting agent is a small molecule, a peptide, or a nucleic acid molecule. The term small molecule in this context is meant to include organic or inorganic compounds (i.e., including heteroorganic and organometallic compounds). A small molecule may be a compound that is less than 2000 daltons in mass, alternatively, the molecular mass of the small molecule is less than 1000 daltons, or less than 600 daltons, e.g., the small molecule is less than 500 daltons, 400 daltons, 300 daltons, 200 daltons, or 100 daltons. Alternatively, the small molecule may have a molecular weight less than about 10,000 grams per mole, or less than about 5,000 grams per mole, or less than about 1,000 grams per mole. In embodiments, a small molecule is an organic or inorganic compound having a molecular weight less than about 500 grams per mole, or less than about 100 grams per mole. Salts, esters, and other pharmaceutically acceptable forms of such compounds are also encompassed.

In embodiments, the F-actin disrupting agent, the microtubule disrupting agent and/or the intermediate filament disrupting agent is a nucleic acid molecule. The nucleic acid molecule may include RNA or DNA. In various embodiments, the nucleic acid molecule may be an inhibitory nucleic acid molecule (e.g., that disrupts the expression or activity of F-actin). In embodiments, the inhibitory nucleic acid is an RNA interfering agent. An RNA interfering agent is any agent that interferes with or inhibits expression of a target gene by RNA interference (RNAi). Such RNA interfering agents include, but are not limited to, peptides, proteins, antisense molecules, ribozymes, small inhibitory nucleic acid sequences, for example but not limited to guide RNAs, small interfering RNA (siRNA), short hairpin RNA or small hairpin RNA (shRNA), a microRNA (miRNA), post-transcriptional gene silencing RNA (ptgsRNA), short interfering oligonucleotides, antisense nucleotides, aptamers. CRISPR RNAs, nucleic acid molecules including RNA molecules which are homologous to the target gene, e.g., a marker of the presently disclosed subject matter, or a fragment thereof, and any molecule which interferes with or inhibit expression of a target gene by RNA interference (RNAi). In embodiments, the inhibitory nucleic acid is a double-stranded RNA, siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule.

In various embodiments, the inhibitory nucleic acid molecule acts at the transcriptional level. In embodiments, the inhibitory nucleic acid molecule is a transcriptional repressor, a nucleic acid sequence that encodes a transcriptional repressor, or an interfering agent involved in the CRISPR (clustered regularly interspaced palindromic repeats) pathway, such as a guide RNA or a CRISPR RNA.

In embodiments, the methods provided herein may be used to increase muscle strength, wherein the muscle strength may be increased by at least about 10% compared to the level of muscle strength prior to contacting the skeletal muscle with an F-actin disrupting agent. In embodiments, the muscle strength may be increased by at least about 2%, at least about 5%, at least about 10%, at least about 12%, at least about 15%, at least about 20%, at least about 30%, at least about 40%, at least about 50%, at least about 60%, at least about 80%, at least about 90%, at least about 95%, at least about 100% compared to the level of muscle strength prior to contacting the skeletal muscle with an F-actin disrupting agent.

In various embodiments, the methods provided herein may be used to increase gait speed or grip strength. In embodiments, the gait speed or grip strength may be increased by at least about 10% compared to the level of gait speed or grip strength prior to contacting the skeletal muscle with an F-actin disrupting agent. In embodiments, the gait speed or grip strength may be increased by at least about 2%, at least about 5%, at least about 10%, at least about 12%, at least about 15%, at least about 20%, at least about 30%, at least about 40%, at least about 50%, at least about 60%, at least about 80%, at least about 90%, at least about 95%, at least about 100% compared to the level of gait speed or grip strength prior to contacting the skeletal muscle with an F-actin disrupting agent.

In aspects, the methods provided herein may be used to increase muscle strength, wherein the muscle strength may be increased about 0.1 to 48 hours post administration. In various aspects, the muscle strength may be increased about 0.1 to 24 hours post administration, about 0.1 to 12 hours post administration, about 0.1 to 11 hours post administration, about 0.1 to 10 hours post administration, about 0.1 to 9 hours post administration, about 0.1 to 8 hours post administration, about 0.1 to 7 hours post administration, about 0.1 to 6 hours post administration, about 0.1 to 5 hours post administration, about 0.1 to 4 hours post administration, about 0.1 to 3 hours post administration, about 0.1 to 2 hours post administration, about 0.1 to 1 hour post administration, or about 0.1 to 0.5 hours post administration.

An effective amount of an F-actin disrupting agent, the microtubule disrupting agent and/or the intermediate filament disrupting agent can be administered once daily, from two to five times daily, up to two times or up to three times daily, or up to eight times daily. In embodiments, the F-actin disrupting agent, the microtubule disrupting agent and/or the intermediate filament disrupting agent is administered thrice daily, twice daily, once daily, fourteen days on (four times daily, thrice daily or twice daily, or once daily) and 7 days off in a 3-week cycle, up to five or seven days on (four times daily, thrice daily or twice daily, or once daily) and 14-16 days off in 3 week cycle, or once every two days, or once a week, or once every 2 weeks, or once every 3 weeks.

Also envisioned are methods comprising combination therapy for the treatment of wasting disorders, heart diseases, or exercise-induced muscle weakness in a subject in need of such treatment. As used herein, "combination therapy" or "co-therapy" includes the administration of an effective amount of a primary therapeutic agent as described herein as part of a specific treatment regimen intended to provide the beneficial effect from the co-action of the primary therapeutic agent and an additional active agent, e.g., an additional active pharmaceutical ingredient (API). The beneficial effect of the combination includes, but is not limited to, pharmacokinetic or pharmacodynamic co-action resulting from the combination of therapeutic compounds. The beneficial effect of the combination may also relate to the mitigation of toxicity, side effect, or adverse event associated with another agent in the combination. "Combination therapy" is not intended to encompass the administration of two or more of these therapeutic compounds as part of separate monotherapy regimens that incidentally and arbitrarily result in a beneficial effect that was not intended or predicted.

The at least one additional active agent may be a therapeutic agent, for example an anti-inflammatory agent, or a non-therapeutic agent, and combinations thereof. With respect to therapeutic agents, the beneficial effect of the combination includes, but is not limited to, pharmacokinetic or pharmacodynamic co-action resulting from the combination of therapeutically active compounds. With respect to nontherapeutic agents, the beneficial effect of the combination may relate to the mitigation of a toxicity, side effect, or adverse event associated with a therapeutically active agent in the combination.

Preferably, the administration of a composition comprising the primary therapeutic agent (i.e., an F-actin disrupting agent, a microtubule disrupting agent and/or an intermediate filament disrupting agent) in combination with one or more additional active agents provides a synergistic response in the subject being treated. In this context, the term "synergistic" refers to the efficacy of the combination being more effective than the additive effects of either single therapy alone. The synergistic effect of a combination therapy according to the disclosure can permit the use of lower dosages and/or less frequent administration of at least one agent in the combination compared to its dose and/or frequency outside of the combination. Additional beneficial effects of the combination can be manifested in the avoidance or reduction of adverse or unwanted side effects associated with the use of either therapy in the combination alone (also referred to as monotherapy).

Pharmaceutical Compositions and Formulations

The present disclosure provides pharmaceutical compositions comprising an amount of a pharmacological agent or a therapeutic agent as described supra. For example, the therapeutic agent may comprise an F-actin disrupting agent, a microtubule disrupting agent and/or an intermediate filament disrupting agent.

A "pharmaceutical composition" is a formulation containing the therapeutic agent in a pharmaceutically acceptable form suitable for administration to a subject. As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. Examples of pharmaceutically acceptable excipients include, without limitation, sterile liquids, water, buffered saline, ethanol, polyol (for example, glycerol, propylene glycol, liquid polyethylene glycol and the like), oils, detergents, suspending agents, carbohydrates (e.g., glucose, lactose, sucrose or dextran), antioxidants (e.g., ascorbic acid or glutathione), chelating agents, low molecular weight proteins, or suitable mixtures thereof.

A pharmaceutical composition can be provided in bulk or in dosage unit form. It is especially advantageous to formulate pharmaceutical compositions in dosage unit form for ease of administration and uniformity of dosage. The term "dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved. A dosage unit form can be an ampoule, a vial, a suppository, a dragee, a tablet, a capsule, an IV bag, or a single pump on an aerosol inhaler.

In therapeutic applications, the dosages vary depending on the agent, the age, weight, and clinical condition of the recipient subject or patient, and the experience and judgment of the clinician or practitioner administering the therapy, among other factors affecting the selected dosage. Generally, the dose should be a therapeutically effective amount. Dosages can be provided in mg/kg/day units of measurement (which dose may be adjusted for the patient's weight in kg, body surface area in $m^2$, and age in years). An effective amount of a pharmaceutical composition is that which provides an objectively identifiable improvement as noted by the clinician or other qualified observer. For example, alleviating a symptom of a disorder, disease or condition. As used herein, the term "dosage effective manner" refers to amount of a pharmaceutical composition to produce the desired biological effect in a subject or cell.

The pharmaceutical compositions can take any suitable form (e.g., liquids, aerosols, solutions, inhalants, mists, sprays; or solids, powders, ointments, pastes, creams, lotions, gels, patches and the like) for administration by any desired route (e.g., pulmonary, inhalation, intranasal, oral, buccal, sublingual, parenteral, subcutaneous, intravenous, intramuscular, intraperitoneal, intrapleural, intrathecal, transdermal, transmucosal, rectal, and the like). For example, a pharmaceutical composition of the disclosure may be in the form of an aqueous solution or powder for aerosol administration by inhalation or insufflation (either through the mouth or the nose), in the form of a tablet or capsule for oral administration; in the form of a sterile aqueous solution or dispersion suitable for administration by either direct injection or by addition to sterile infusion fluids for intravenous infusion; or in the form of a lotion, cream, foam, patch, suspension, solution, or suppository for transdermal or transmucosal administration.

In further embodiments, the compositions may comprise of inducible actin disrupting plasmids or viruses.

In some examples, the F-actin disrupting agent, the microtubule disrupting agent and/or the intermediate filament disrupting agent can be encapsulated for the targeted delivery to specific organs (e.g., skeletal muscle muscle). A variety of means for encapsulation of the F-actin disrupting agent are contemplated. Some examples include, but not limited to targeted nanoparticles, nanocarriers, liposomes, endosomes, adenoviruses, and the like that enable release of the F-actin disrupting agent into the specific organ (e.g., skeletal muscle, or in other embodiments can include smooth muscle).

A pharmaceutical composition may be in a form suitable for administration by inhalation, for example as an aqueous or non-aqueous aerosol, or as a dry powder. In embodiments, the pharmaceutical composition is an aqueous solution adapted for delivery via a nebulizer, including jet, vibrating mesh, and static mesh or orifice nebulizers. In embodiments, the pharmaceutical composition is a dry powder adapted for delivery via a dry powder inhaler device.

A pharmaceutical composition can be in the form of an orally acceptable dosage form including, but not limited to, capsules, tablets, buccal forms, troches, lozenges, and oral liquids in the form of emulsions, aqueous suspensions, dispersions or solutions. Capsules may contain mixtures of a compound of the present disclosure with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc. In the case of tablets for oral use, carriers which are commonly used include lactose and corn starch. Lubricating agents, such as magnesium stearate, can also be added. For oral administration in a capsule form, useful diluents include lactose and dried corn starch. When aqueous suspensions and/or emulsions are administered orally, the compound of the present disclosure may be suspended or dissolved in an oily phase is combined with emulsifying and/or suspending agents. If desired, certain sweetening and/or flavoring and/or coloring agents may be added.

A pharmaceutical composition can be in the form of a tablet. The tablet can comprise a unit dosage of a compound of the present disclosure together with an inert diluent or carrier such as a sugar or sugar alcohol, for example lactose, sucrose, sorbitol or mannitol. The tablet can further comprise a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. The tablet can further comprise binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures.

The pharmaceutical compositions for use in the methods of the present disclosure can further comprise one or more additives in addition to any carrier or diluent (such as lactose or mannitol) that is present in the formulation. The one or more additives can comprise or consist of one or more surfactants. Surfactants typically have one or more long aliphatic chains such as fatty acids which enables them to insert directly into the lipid structures of cells to enhance drug penetration and absorption.

Administration of Pharmacological Agents or Therapeutic Agents

The pharmacological agent or the therapeutic agent is administered to a subject with diseased or functionally compromised skeletal or smooth muscle or to a healthy subject who wishes to augment their muscle strength. In some examples, the subject comprises a muscle wasting disorder, a muscle degenerative disease, or an exercise-induced muscle weakness. Alternatively, the diseased or functionally compromised skeletal muscle is the result of a muscle wasting disorder, cancer, or exercise-induced muscle weakness. In other aspects, the pharmacological agent or the therapeutic agent may be administered to a healthy subject, e.g., wherein the skeletal or smooth muscle is not functionally compromised or diseased. In this population, the subjects may wish to amplify their strength. In other examples, the pharmacological agent or the therapeutic agent may be administered to a subject t has not been diagnosed with a cancer.

The pharmacological agent or the therapeutic agent may be administered at a doses that are therapeutically insufficient as an anticancer agent. For example, breast cancer patients prescribed paclitaxel are administered about 175 mg/m$^2$ (e.g., via intravenous administration). As described herein, the subject may be administered a pharmacological agent or a therapeutic agent of the invention that would be therapeutically insufficient as an anticancer agent, e.g., less than the defined dosage (for example, less than 175 mg/m$^2$ as described above for breast cancer patients taking paclitaxel). Other exemplary dosages of paclitaxel include: non-small cell lung cancer (135 mg/m$^2$), AIDS-related Kaposi's Sarcoma (135 mg/m$^2$ or 100 mg/m$^2$), pancreatic cancer (125 mg/m$^2$), and hepatic impairment (50-135 mg/m$^2$). The pharmacological agent or the therapeutic agents described herein may be administered in dosages that would be ineffective as anticancer agents.

In other examples, the chemotherapeutic dosage range (e.g., the TAXOL™ class of compounds and their derivatives thereof) may be in the high mg/mL range (e.g., about 10 mg/mL for carboplatin and about 6 mg/mL for paclitaxel). See, e.g., Akin, J, et al., "Cancer Chemotherapy Update: Paclitaxel and Carboplatin (TC) Regimen for Ovarian Cancer." *Hosp Pharm* 2014; 49(5): 425-31, incorporated herein by reference in its entirety. As described herein, the pharmacological agent or the therapeutic agent may be administered at doses insufficient as an anticancer agent (e.g., the dose may be lower than their ability to act as an anticancer agent). Thus, low mg/mL concentrations are contemplated. For example, concentrations less than about 5 mg/ml, less than about 4 mg/mL, less than about 3 mg/mL, less than about 2 mg/mL, less than about 1 mg/mL, less than about 0.5 mg/mL, less than about 0.1 mg/mL, less than about 0.01 mg/mL, or less than about 0.001 mg/mL are contemplated. Alternatively, the pharmacological agent or the therapeutic agent may be at a concentration of about 0.001 mg/mL to about 5 mg/mL, or from about 0.01 mg/mL to about 5 mg/mL, or from about 0.1 mg/mL to about 5 mg/mL, or from about 0.5 mg/mL to about 5 mg/mL, or from about 1 mg/mL to about 5 mg/mL, or from about 2 mg/mL to about 5 mg/mL, or from about 3 mg/mL to about 5 mg/mL, or from about 4 mg/mL to about 5 mg/mL.

EXAMPLES

The following examples are put forth so as to provide those of ordinary skill in the art with a complete disclosure and description of how to make and use the methods of the invention, and are not intended to limit the scope of what the inventors regard as their invention.

Example 1: Differentiated Skeletal Muscle Tissue and Contractility

Figure 5A:
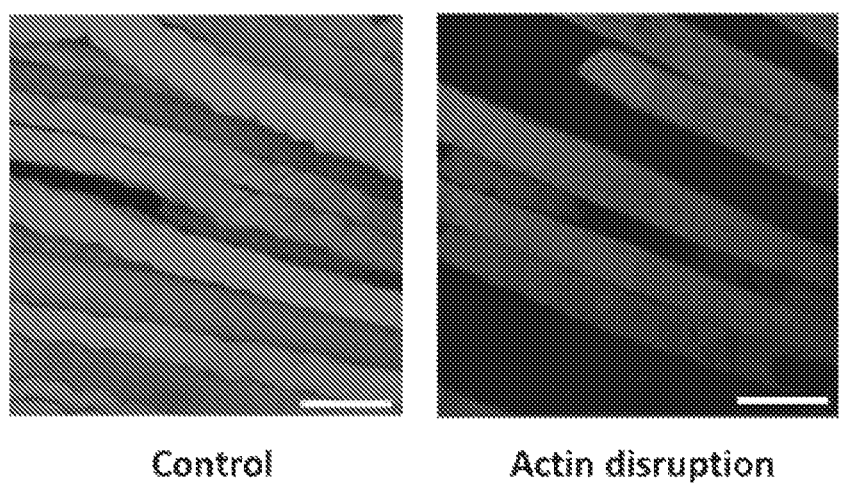
FIG. 5A is an image showing phalloidin stain that revealed F-actin in mouse EDL muscle, using cytochalasin D (Zygosporin A and cytochalasin D are synonymous) for actin disruption.
Figure 5B:
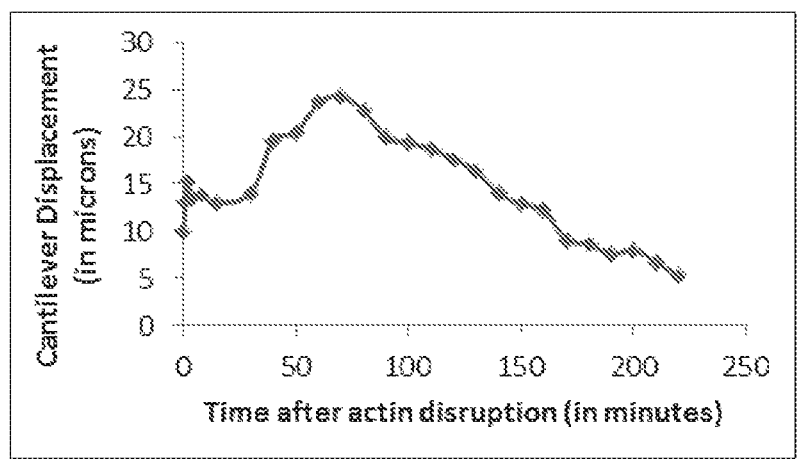
FIG. 5B is a graph showing cantilever displacement versus time after actin disruption using cytochalasin (e.g. Zygosporin A).
Figure 5C:
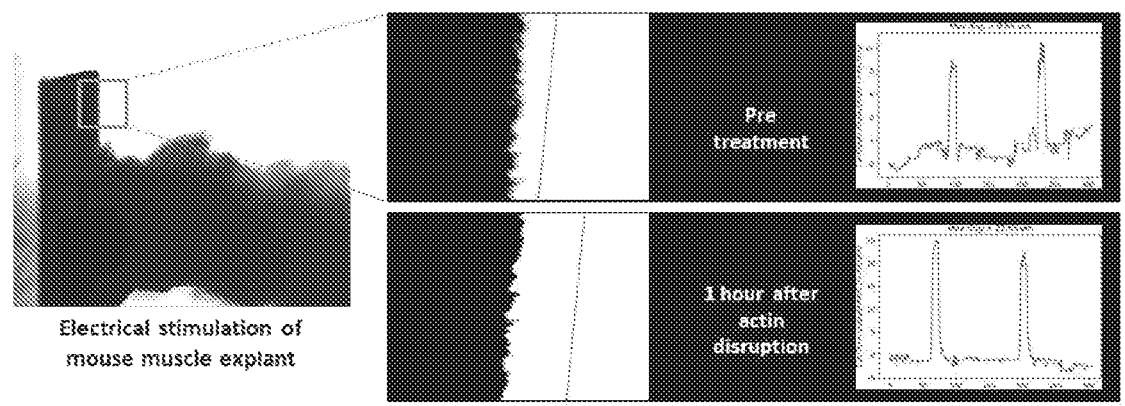
FIG. 5C is an image showing the electrical stimulation of mouse muscle explant, pre-treatment and 1 hour after actin disruption using cytochalasin (e.g. Zygosporin A). F-actin disruption improved contractility of mouse hindlimb EDL muscle explant.
Figure 6:
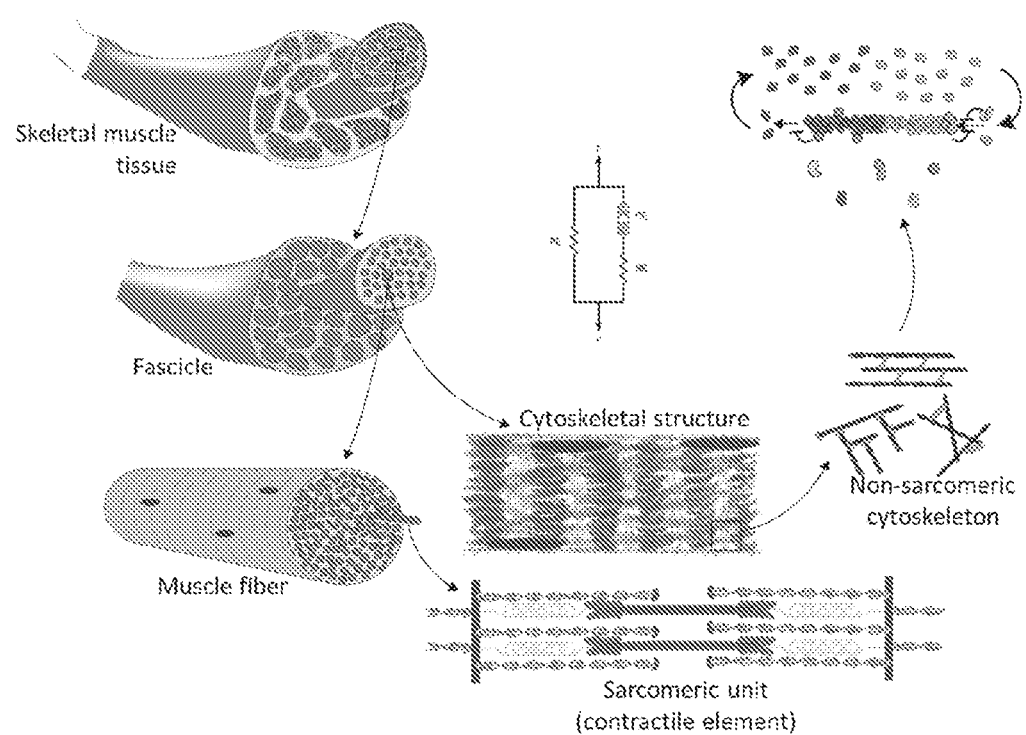
FIG. 6 is diagram depicting a conceptual model of non-sarcomeric actin as a target to improve muscle contractility and visualization of actin disruption. Multiscale bio-mechanical model of skeletal muscle tissue with a parallel elastance (PE) and a serial elastance (SE). Lowering PE by disrupting F-actin lead to improved contractility.

An in vitro optogenetic skeletal muscle micro-tissue as a model system (e.g., engineered skeletal muscle) such as the one shown in FIG. 1A-1E was used. Briefly, a sacrificial molding technique was used to form the muscle tissue on the cantilevers. A steel rod was used to mold a cylindrical hole in solidified gelatin. The steel rod was then removed and myoblasts in an extracellular matrix material was inserted in its place. The myoblasts were then differentiated in place to form a differentiated muscle tissue. With this system, a range of actin inhibitors were tested (e.g., Cytochalasin D (Zygosporin A), Latrunculin A, SMIFH2, CK666 and Jasplakinode) including ones that bind to the barbed end of F-actin, ones that sequester G-actin monomers and inhibitors of formins, roughly a 100% increase in muscle strength was observed (FIGS. 2A-2B and FIGS. 3A-3B) and a 300% increase in external work performed was observed, within 2 hours of F-actin disruption. Additionally, disruption of the dynamic F-actin cytoskeleton using small molecule actin dynamics inhibitors led to a persistent 2-fold improvement in force (e.g., muscle performance or work) compared to exercising (FIG. 4A-4E). Actin disruption improved mouse muscle explant force, a model system that is very close to human muscle (FIG. 5A-5C).

Biomechanical testing at the cell level, using atomic force microscopy (AFM), and at the tissue level using a microtensile test showed a drop in mechanical stiffness that correlated well with improvement in muscle work. Using plasmids that genetically encoded actin disruption using truncated versions of endogenous proteins, the cytoskeletal resistance/contractility knob was tuned in a dose-dependent and inducible manner.

A 3-D printed biobot-based walking assay showed that a weak limping biobot started walking robustly after F-actin disruption.

Translation of these results was shown in an ex vivo mouse muscle model.

An analysis of the actin dynamics using fluorescence recovery after photobleaching (FRAP) in a GFP-actin transfected myotube revealed that actin disruption had a persistent impact due to intracellular G-actin protein depletion. This data was confirmed by Western blot analysis.

The mechanobiological gene expression changes introduced by altering F-actin dynamics were evaluated using qPCR as well as through Western analysis which showed activation of the AKT/mTOR pathway which activated protein production in muscle.

Targeting of dynamic F-actin as a therapeutic target in human engineered skeletal muscle as well as smooth muscle is evaluated.

Potential tradeoffs involved in F-actin disruption were evaluated, which revealed the role of the dynamic F-actin in sarcomeric alignment, mechanical rigidity, fatigue resistance and cellular metabolism.

Figure 7A:
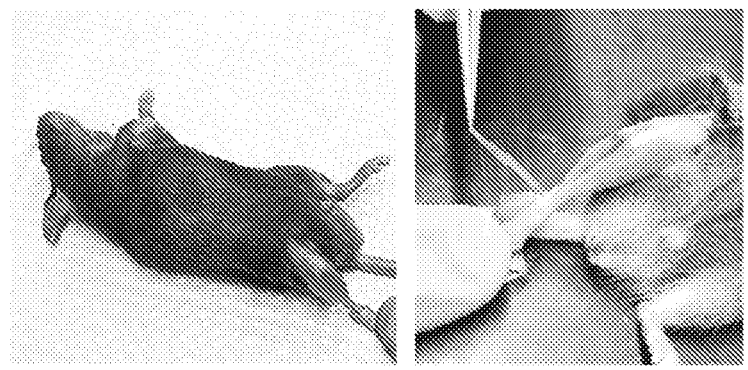
FIG. 7A is an image showing a dissected hindlimb extensor digitorum longus (EDL) muscle of a euthanized 2-3 month old male mouse.
Figure 7B:
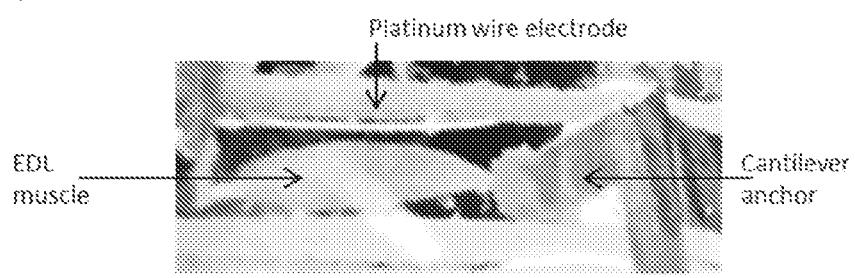
FIG. 7B is an image showing the EDL muscle anchored between two kapton cantilevers using a cyanoacrylate glue.
Figure 7C:
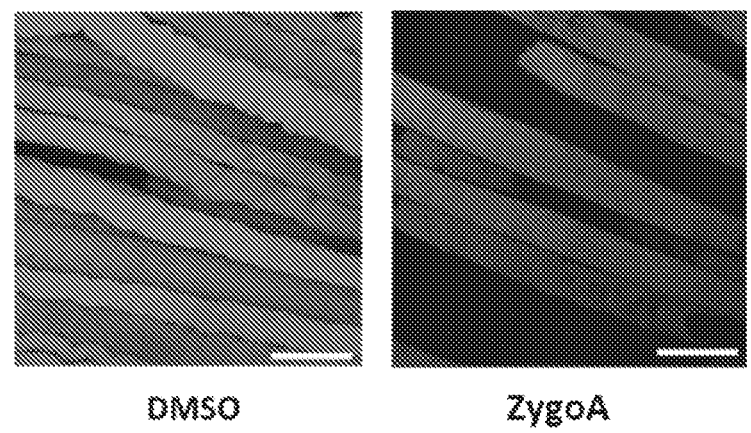
FIG. 7C is an image depicting that Zygosporin A (ZygoA) disrupted F-actin in the muscle explants as shown in the phalloidin stained samples after 2 hours of treatment with 3 uM ZygoA or DMSO.

Example 2: Actin Disruption Lead to a Transient Increase in Mouse Hindlimb Explant Contractility The hindlimb extensor digitorum longus (EDL) muscle of a euthanized 2-3 month old male mouse was dissected. The EDL muscle was anchored between two kapton cantilevers using a cyanoacrylate glue. One of the cantilevers was movable whose position could be adjusted to change the resting tension of the muscle. The cantilever was moved to the point where maximal force was produced and was held at this point for the rest of the experiment. (FIG. 7A-7B). Zygosporin A (ZygoA) disrupted F-actin in the muscle explants as shown in the phalloidin stained samples after 2 hours of treatment with 3 uM ZygoA or DMSO (FIG. 7C).

Figure 7D:
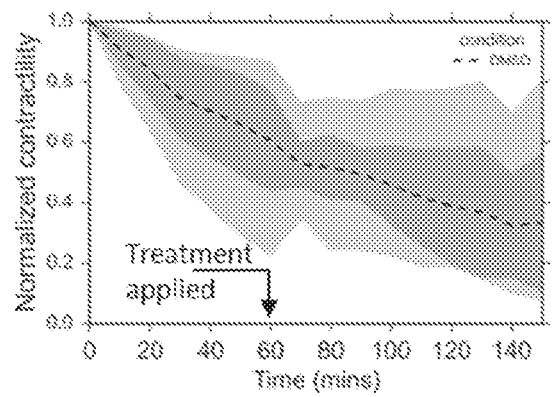
FIG. 7D is a graph depicting the comparison of contractility changes of DMSO treated tissues (treatment at t=60 mins)
Figure 7E:
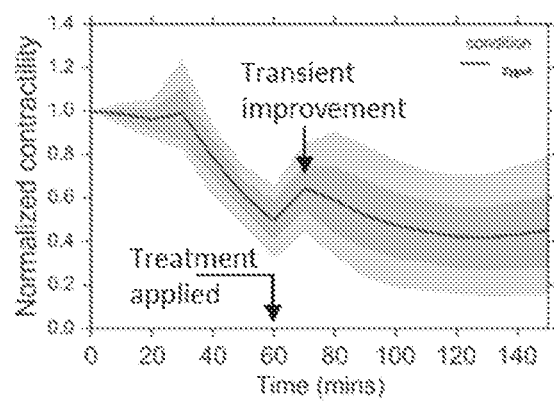
FIG. 7E is a graph depicting the comparison of contractility changes of ZygoA treated tissues (treatment at t=60 mins) showed a transient improvement in ZygoA treated tissues before rigor mortis lead to functional decline of the tissue.
Figure 7F:
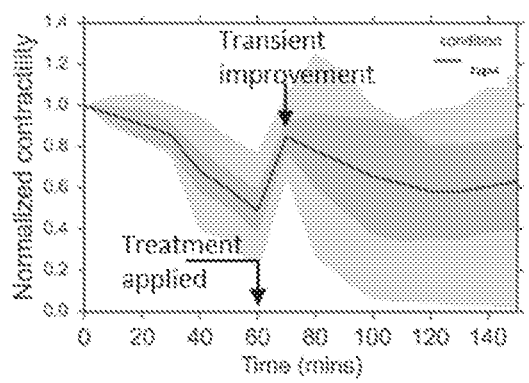
FIG. 7F is a graph depicting ZygoA treated tissues that responded the best, with an average of ~2× transient increase in contraction after treatment, followed by decline.
Figure 7G:
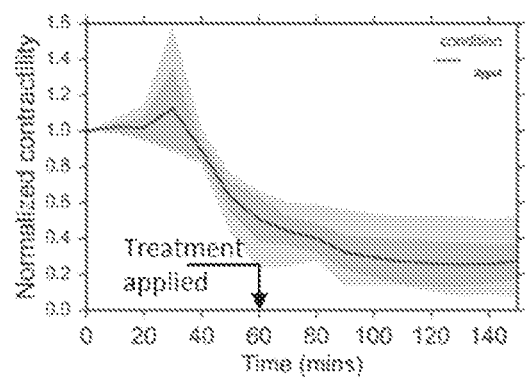
FIG. 7G is a graph depicting ZygoA treated tissues that die rapidly and did not show any transient improvement.
Figure 7H:
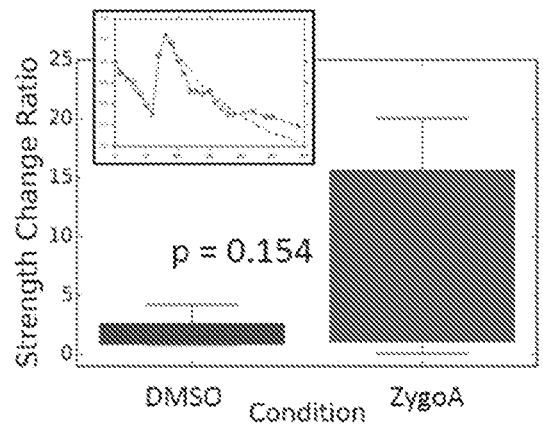
FIG. 7H is a graph showing the modeling of the decline associated with rigor mortis as an exponential decay lets us estimate the "true" strength change after treatment. The muscle strength of tissue after treatment extrapolated was compared to time t=0 and this was represented as a strength ratio relative to the actual strength at t=0. ZygoA treated tissues showed a ~2.5-fold increase in median strength ratio relative to DMSO treated controls.

Comparison of contractility changes of DMSO and ZygoA treated tissues (treatment at t=60 mins) showed a transient improvement in ZygoA treated tissues before rigor mortis leads to functional decline of the tissue. None of the DMSO treated tissues show any such transient improvement. The two colored envelopes around the curves representing the mean are the 68% and 95% confidence interval envelopes (FIG. 7D). ZygoA treated tissues that responded the best, with an average of ~2× transient increase in contraction after treatment, followed by decline (FIG. 7E). ZygoA treated tissues that died rapidly did not show any transient improvement (FIG. 7F). Modeling the decline associated with rigor mortis as an exponential decay estimated the "true" strength change after treatment. The muscle strength was compared of tissue after treatment extrapolated to time t=0 and represent this as a strength ratio relative to the actual strength at t=0. ZygoA treated tissues show a ~2.5-fold increase in median strength ratio relative to DMSO treated controls.

Figure 8A:
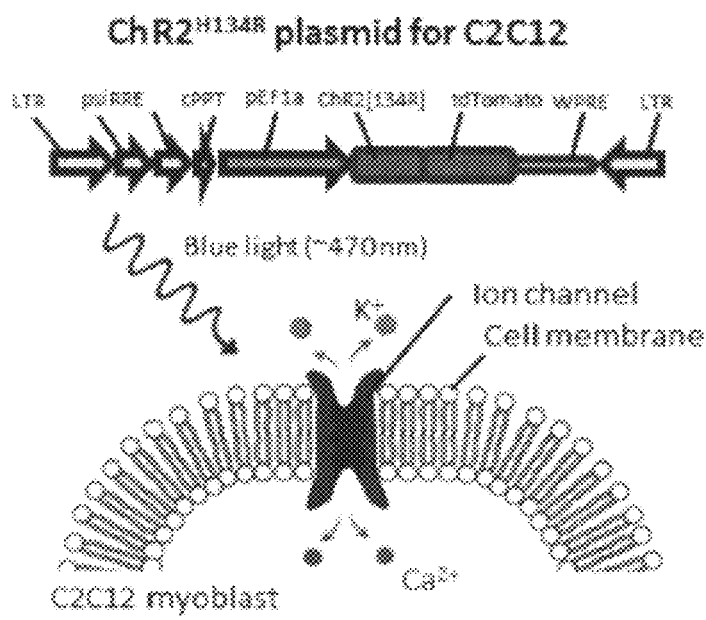
FIG. 8A is a diagram depicting the construction of an optogenetic transgenic C2Cl2 myoblast cell line.
Figure 8B:
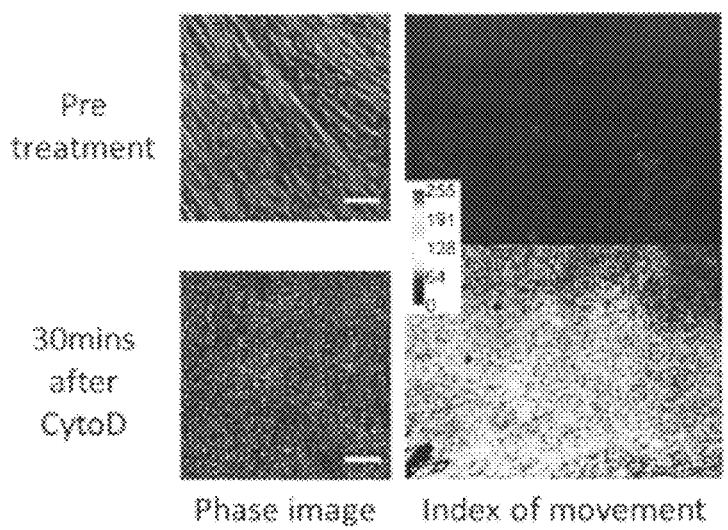
FIG. 8B is an image depicting ZygoA treatment of differentiated C2Cl2 myotubes that lead to a significant improvement in active contraction as quantified by changes in the Index of Movement as shown in the colormap (bottom right)
Figure 8C:
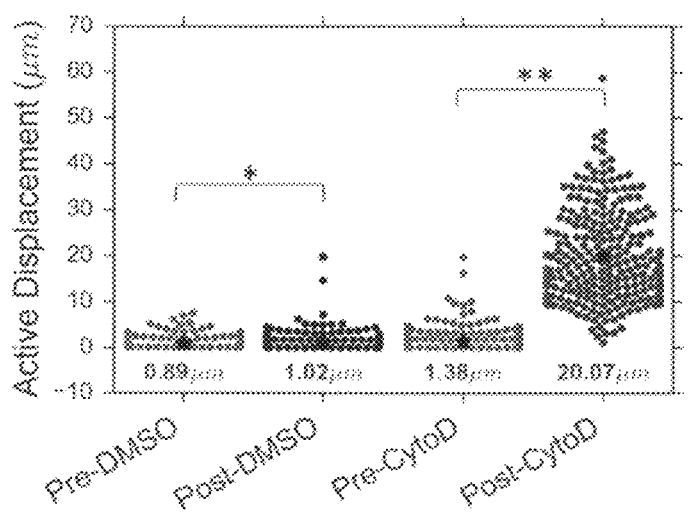
FIG. 8C is a graph showing the increase in active contractile displacement.
Figure 8D:
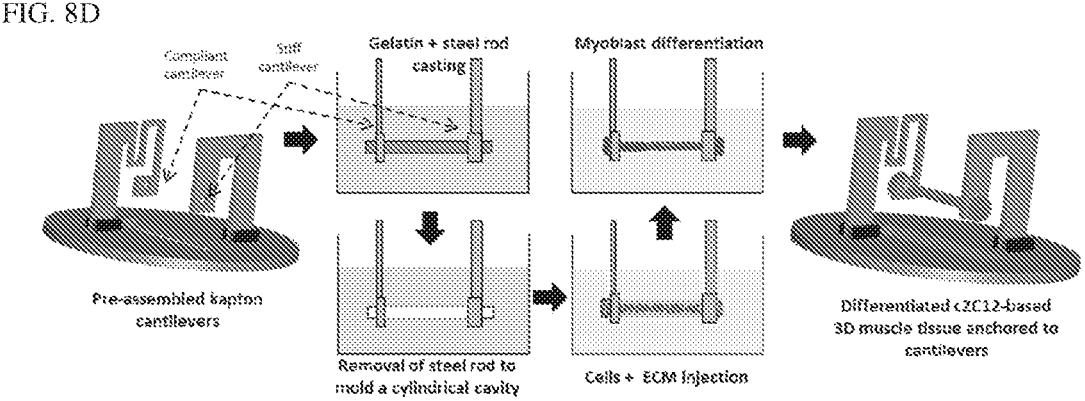
FIG. 8D is a schematic showing the fabrication of a 3D engineered skeletal muscle tissue by differentiating C2Cl2 myoblasts mixed in a fibrin/matrigel extracellular matrix cast in to a muscle-like cylindrical shape using a sacrificial molding technique. The muscle tissue is anchored to a stiff cantilever and a more compliant cantilever.
Figure 8E:
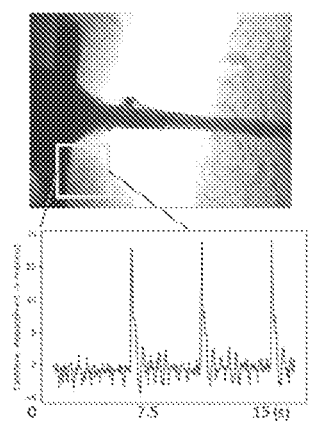
FIG. 8E is an image showing the optogenetic stimulation of the muscle tissue that lead to muscle contraction.
Figure 8F:
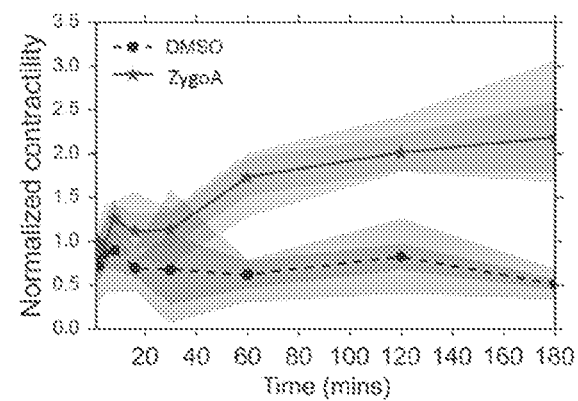
FIG. 8F is a graph showing the quantification of the optogenetic stimulation of the muscle tissue (from FIG. 8E) through measurable displacements of the compliant cantilever.
Figure 8G:
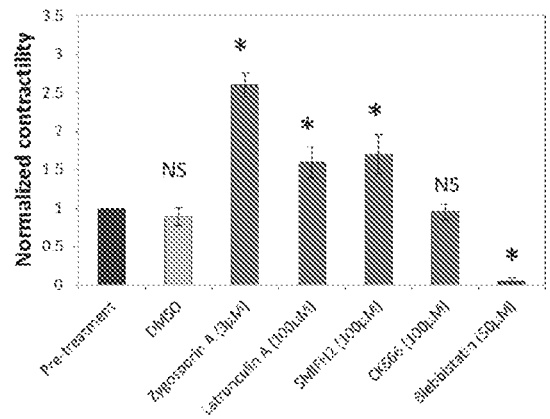
FIG. 8G is a bar graph showing that the treatment of the 3D muscle with several other actin disrupters (Latrunculin A, SMIFH2) also improved muscle contraction, indicating that F-actin disruption improved muscle contraction (as opposed to non-specific effects of ZygoA).

Example 3: F-Actin Disruption Leads to an Improvement in In Vitro Engineered Skeletal Muscle Contraction Construction of optogenetic transgenic C2Cl2 myoblast cell line and Cyto D (e.g., Zygo A) treatment of differentiated C2Cl2 myotubes lead to a significant improvement in active contraction as quantified by changes in the Index of Movement as shown in the colormap and increased in active contractile displacement (FIG. 8A-8C). Fabrication of a 3D engineered skeletal muscle tissue by differentiating C2Cl2 myoblasts mixed in a fibrin/matrigel extracellular matrix cast in to a muscle-like cylindrical shape using a sacrificial molding technique. The muscle tissue is anchored to a stiff cantilever and a more compliant cantilever. Optogenetic stimulation of the muscle tissue lead to muscle contraction which was quantified through measurable displacements of the compliant cantilever. ZygoA treatment of the 3D muscle tissues lead to a significant improvement in contraction relative to DMSO treated controls, reaching ~2-fold increase in 2 hours. Treatment of the 3D muscle with several other actin disrupters (Latrunculin A, SMIFH2) also improved muscle contraction, indicated that F-actin disruption in general improves muscle contraction (as opposed to non-specific effects of ZygoA) (FIG. 8D-G).

Figure 9A:
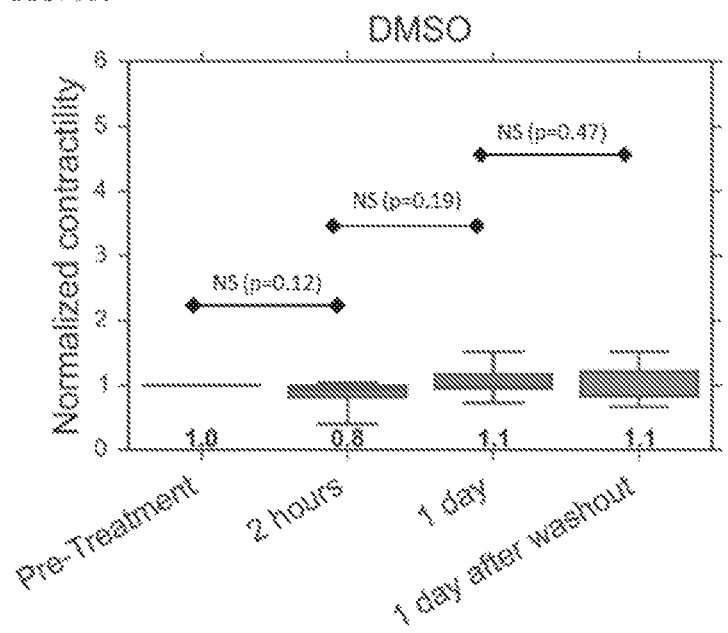
FIG. 9A is a graph showing that DMSO treated controls had no significant effect on muscle active contraction at either short (2 hours of exposure) or long term (1 day).
Figure 9B:
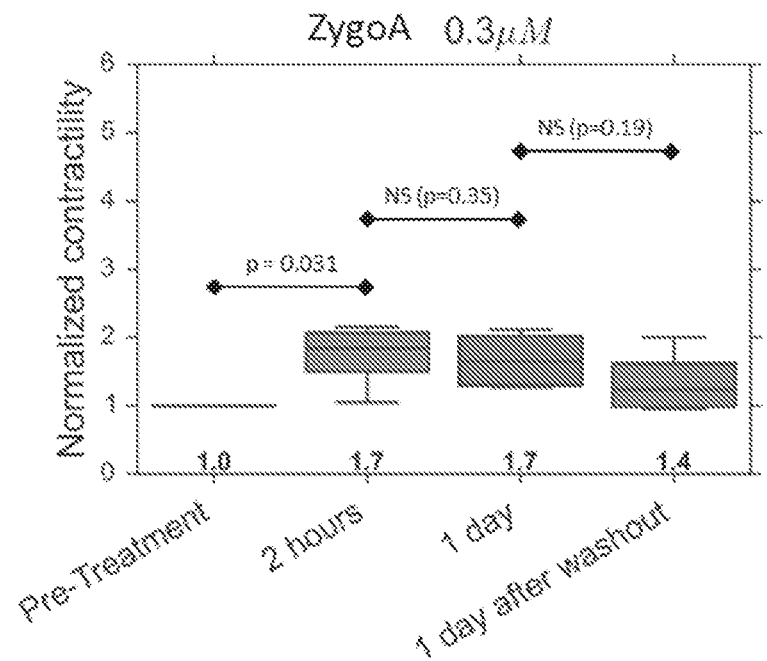
FIG. 9B is a graph showing that the short term response to ZygoA treatment showed a monotonic improvement in force with the extent of actin disruption approximately 1.7× increase with 0.3 µM ZygoA and 2.6× increase with 3 µM ZygoA.
Figure 9C:
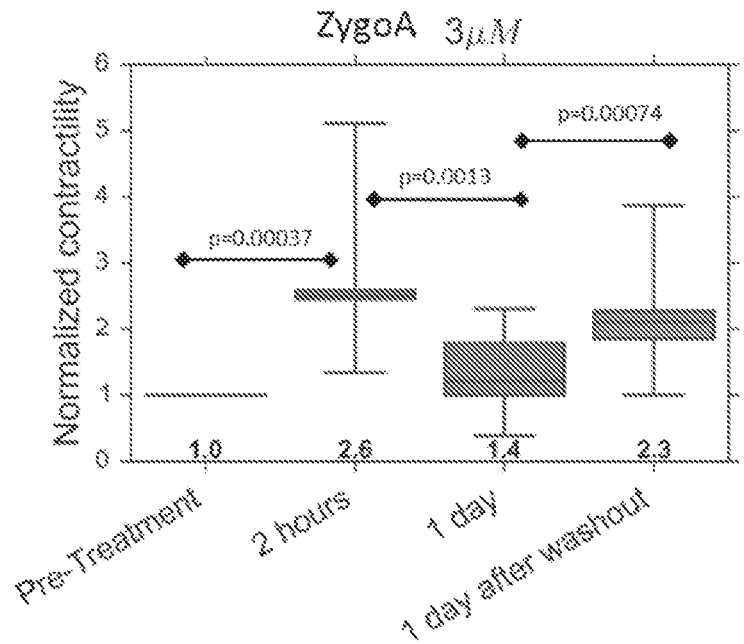
FIG. 9C is a graph showing that the higher dose ZygoA (3 µM) lead to a ~50% decrease in contraction compared to the peak of 2.6× achieved 2 hours after ZygoA exposure.
Figure 9D:
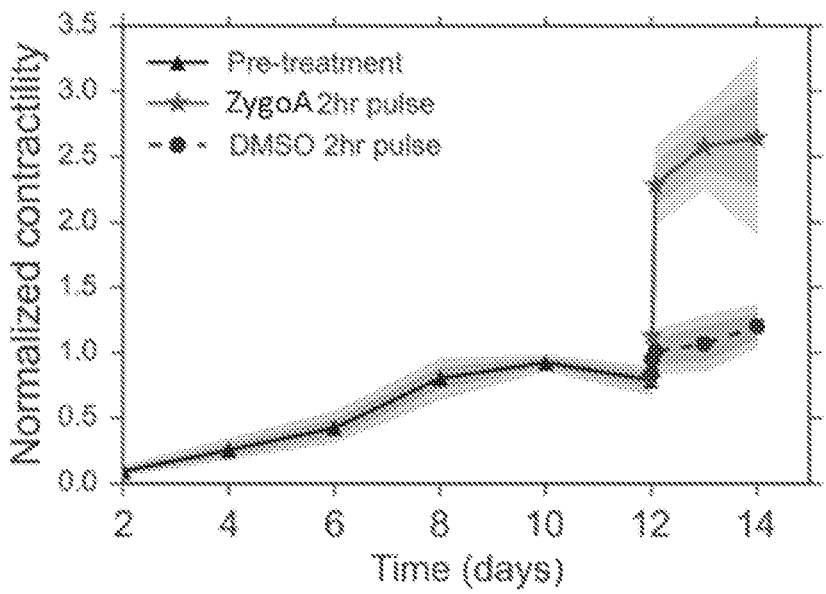
FIG. 9D is a graph showing that a high dose ZygoA had a deleterious effect with longer term exposure. A quick pulsed treatment of the muscle with ZygoA (3 µM) for 2 hours followed by a washout was considered which lead to a sustained improvement in muscle contraction compared to DMSO treated controls even days after washout of ZygoA.

Example 4: Actin Disruption with ZvgoA had a Dose-Dependent Effect on In Vitro Muscle Active Contractility, with Different Short and Long Term Behavior DMSO treated controls had no significant effect on muscle active contraction at either short (2 hours of exposure) or long term (1 day). The short term response to ZygoA treatment showed a monotonic improvement in force with the extend of actin disruption ~1.7× increase with 0.3 μM ZygoA and 2.6× increase with 3 uM ZygoA (FIG. 9A-9C). At longer term, the low dose ZygoA (0.3 μM) has no significant effect (FIG. 9B). However, the higher dose ZygoA (3 μM) lead to a ~50% decrease in contraction compared to the peak of 2.6× achieved 2 hours after ZygoA exposure (FIG. 9C). Washout of low dose ZygoA (0.3 uM) lead to a slight decrease in contraction (not significant) perhaps due to F-actin repolymerization. On the contrary, washout of high dose ZygoA (3 uM) lead to a recovery of the force to the level of the peak achieved 2 hours after exposure. As high dose ZygoA seemed to have a deleterious effect with longer term exposure, a quick pulsed treatment was considered of the muscle with ZygoA (3 uM) for 2 hours followed by a washout. This lead to a sustained improvement in muscle contraction compared to DMSO treated controls even days after washout of ZygoA (FIGS. 9C and 9D).

Figure 10A:
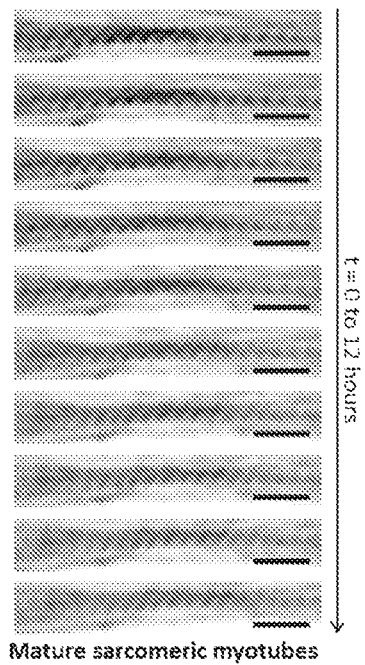
FIG. 10A is an image depicting that myotubes with a mature sarcomeric F-actin structure still displayed the periodic sarcomeric structure 12 hours after ZygoA treatment. Some background non-sarcomeric F-actin was depolymerized (FIG. 10A) as also quantified in (FIG. 10D).
Figure 10B:
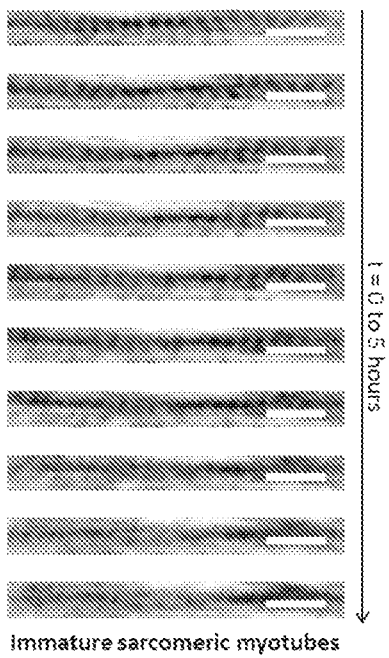
FIG. 10B is an image depicting that myotubes with an immature sarcomeric structure were depolymerized ~5 hours after ZygoA treatment.

Example 5: Visualization of Changes in F-Actin Structure Due to Actin Disruption with Live Confocal Time-Lapse Microscopy Myotubes pre-incubated with 100 nM Sir-Actin, a fluorescent dye that binds to F-actin helped visualize F-actin structures, with Sir-Actin intensity displayed as shades of grey in the figure (FIG. 10A-10E), 0.3 uM ZygoA was used for F-actin disruption. Myotubes with a mature sarcomeric F-actin structure displayed the periodic sarcomeric structure 12 hours after ZygoA treatment. However, some of the background non-sarcomeric F-actin was depolymerized as also quantified in (FIG. 10D). Myotubes with an immature sarcomeric structure were depolymerized ~5 hours after ZygoA treatment (FIG. 10C). Poorly differentiated, myotubes without visible sarcomeric structures had rupturing F-actin cables and significant actin upon actin disruption with ZygoA. Quantifying this showed a decrease in the average F-actin filament length as well as an increase in number of F-actin filaments. Sir-Actin intensity before and 12 hours after treatment along sarcomeric F-actin in mature myotubes (FIG. 10D-10E).

Figure 11A:
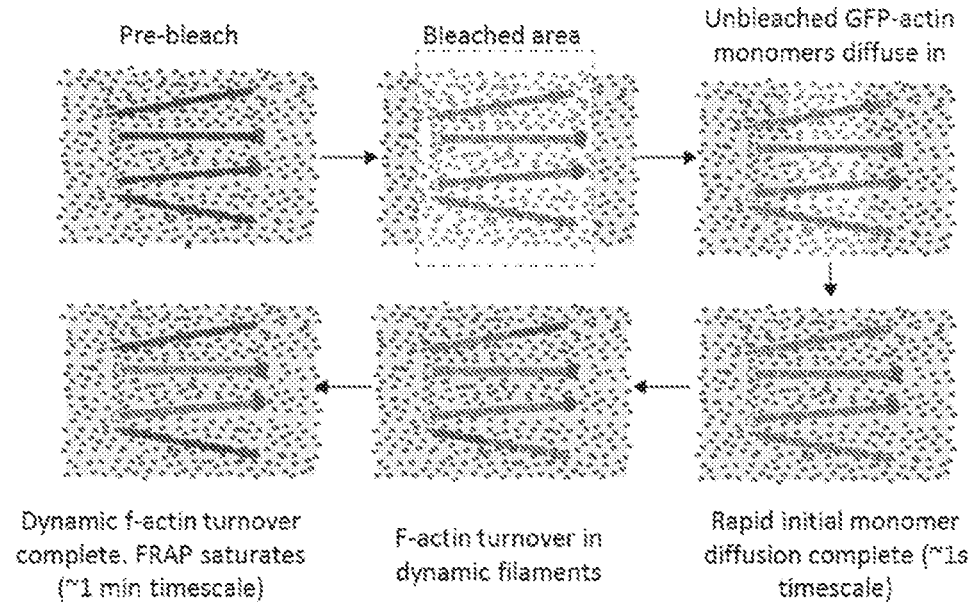
FIG. 11A is an image depicting that the fluorescence recovery in differentiated myotubes is affected by 3 different events: diffusion, dynamic F-actin turnover and stable F-actin turnover as also illustrated in FIG. 1C.
Figure 11B:
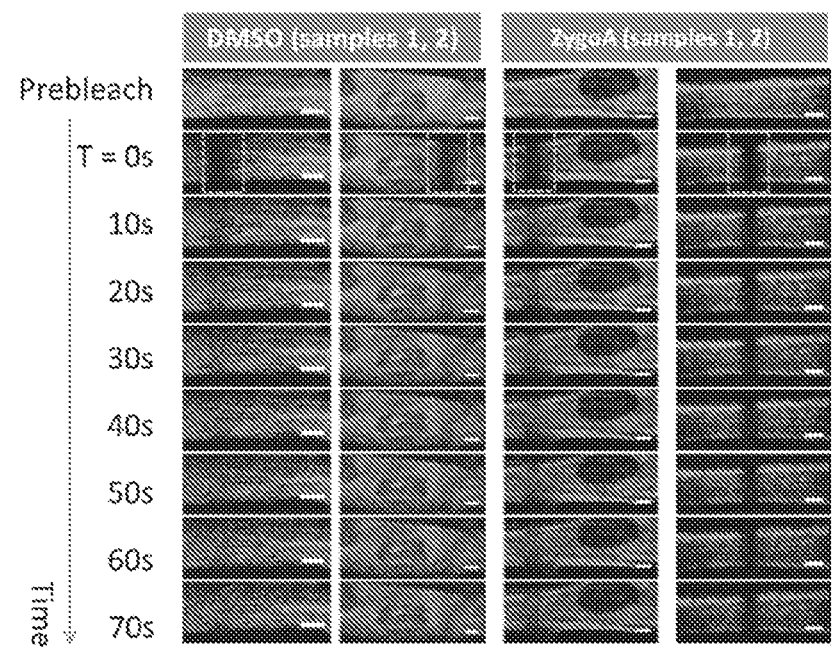
FIG. 11B is an image depicting that DMSO treated tissues recovered faster than ZygoA treated tissues.
Figure 11C:
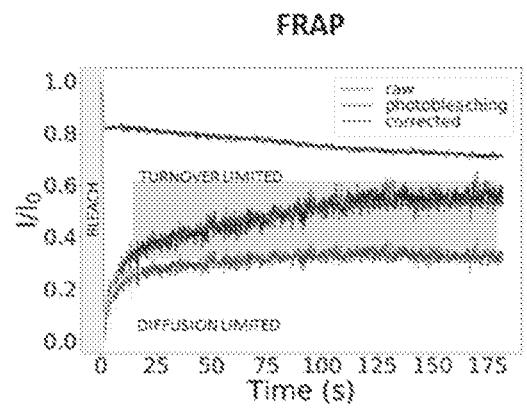
FIG. 11C is an image depicting that the fluorescence recovery at different timescales.
Figure 11D:
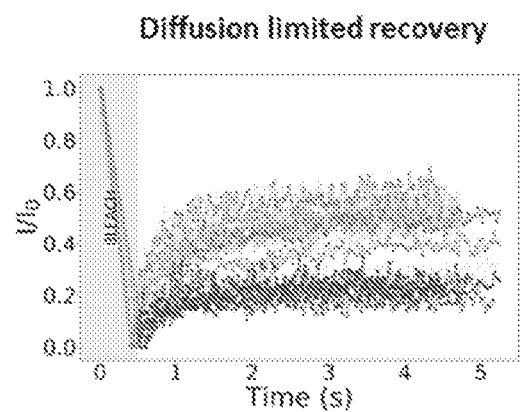
FIG. 11D is an image depicting diffusion limited recovery.
Figure 11E:
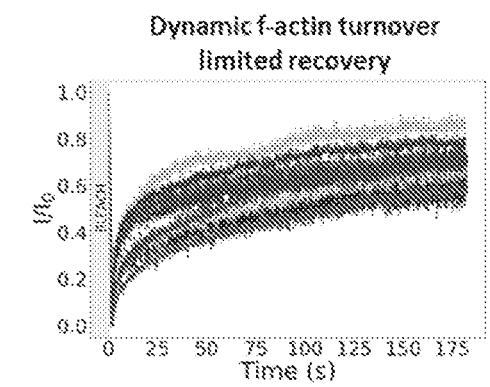
FIG. 11E is an image depicting dynamic F-actin turnover limited recovery.
Figure 11F:
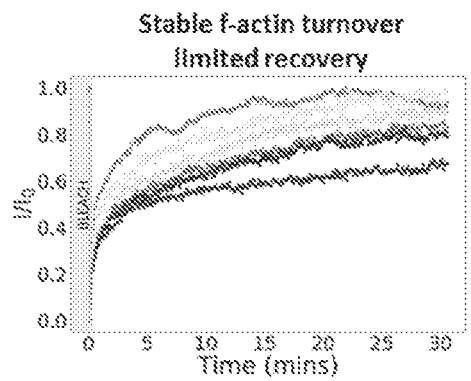
FIG. 11F is an image depicting stable F-actin turnover limited recovery.
Figure 11G:
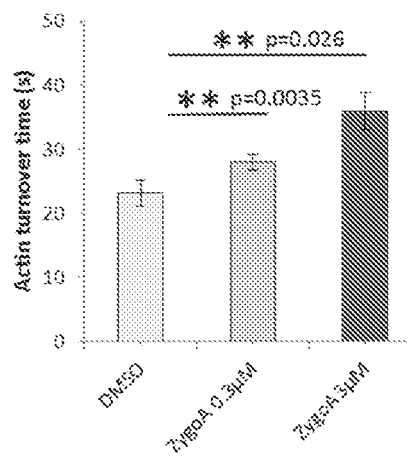
FIG. 11G is a bar graph depicting that ZygoA treatment slowed the actin turnover time in a dose-dependent manner which reflected the mechanism of action of ZygoA that binds to the barbed end of F-actin slowing down actin turnover.
Figure 11H:
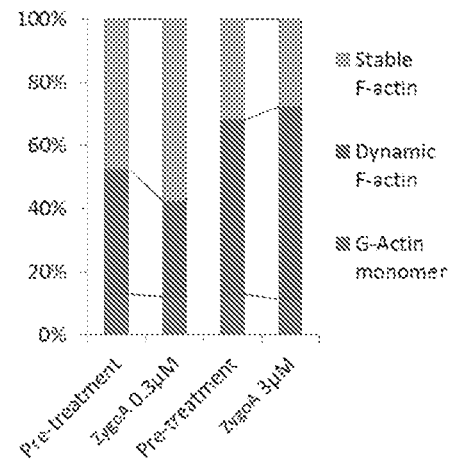
FIG. 11H is a graph depicting that low dose ZygoA (0.3 µM) reduced the amount of dynamic F-actin, while higher dose ZygoA (3 µM) reduces the amount of stable F-actin. Changes in dynamic and stable F-actin fractions were statistically significant.

Example 6: Fluorescence Recovery after Photobleaching of GFP-Tagged G-Actin in C2Cl2 Myotubes Helped Correlate the Dose-Response of ZygoA to Specific Compartments of F-Actin The fluorescence recovery in differentiated myotubes was affected by 3 different events: diffusion, dynamic F-actin turnover and stable F-actin turnover. DMSO treated tissues recovered faster than ZygoA treated tissues. Some ZygoA treated tissues did not recover at all, as the myotubes tore apart in the 2D myotube assay (FIG. 11A-11C). These myotubes were excluded from the computation. Fluorescence recovery at different timescales (seconds, minutes, tens of minutes) reflected different molecular processes (diffusion of monomer, dynamic F-actin turnover, stable F-actin turnover). ZygoA treatment slowed the actin turnover time in a dose-dependent manner which reflected the mechanism of action of ZygoA that bound to the barbed end of F-actin slowing down actin turnover. Low dose ZygoA (0.3 uM) reduced the amount of dynamic F-actin, while higher dose ZygoA (3 uM) reduced the amount of stable F-actin. Changes in dynamic and stable F-actin fractions were statistically significant (FIG. 11D-11E).

Example 7: The Contractility Improvement Due to F-Actin Disruption was Mostly a Mechanical Effect Due to Reduction in Internal Mechanical Resistance from the F-Actin AFM testing of differentiated myotubes showed a decrease in apparent elastic modulus of the myotubes.

Figure 12A:
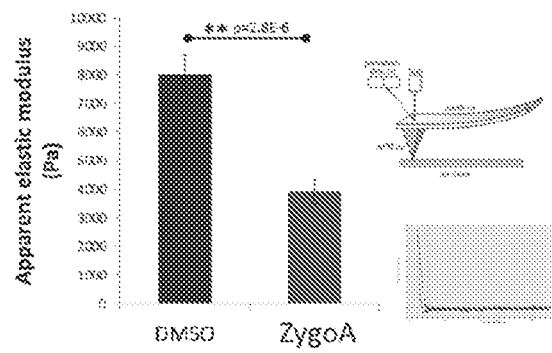
FIG. 12A is a bar graph depicting that AFM testing of differentiated myotubes showed a decrease in apparent elastic modulus of the myotubes.
Figure 12B:
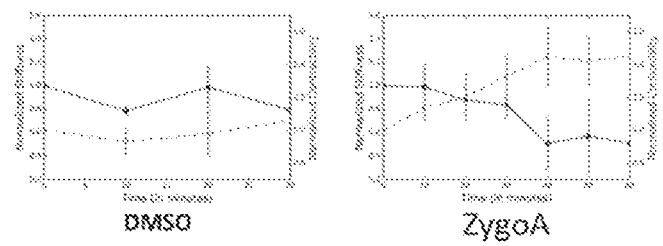
FIG. 12B are graphs showing that tissue level micro-tensile testing showed a decrease in axial stiffness at the same timescale as an increase in active contraction.
Figure 12C:
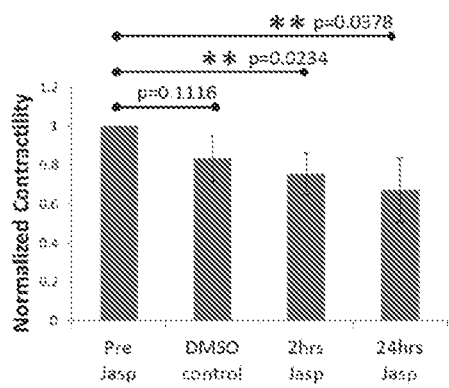
FIG. 12C is a bar graph showing F-actin stabilization by jasplakinolide lead to a gradual decrease in active contractility, showing that the opposite of F-actin disruption lead to the functionally opposite response of force improvement.
Figure 12D:
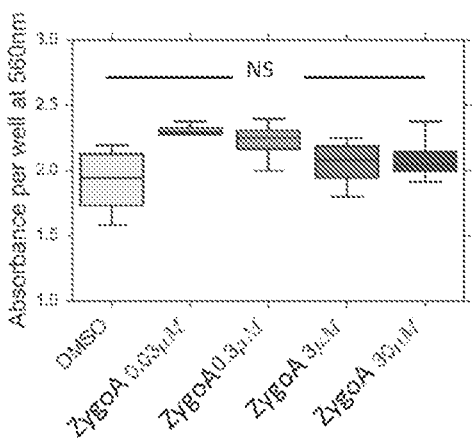
FIG. 12D is a graph showing that actin disruption did not change mitochondrial enzymatic activity.
Figure 12E:
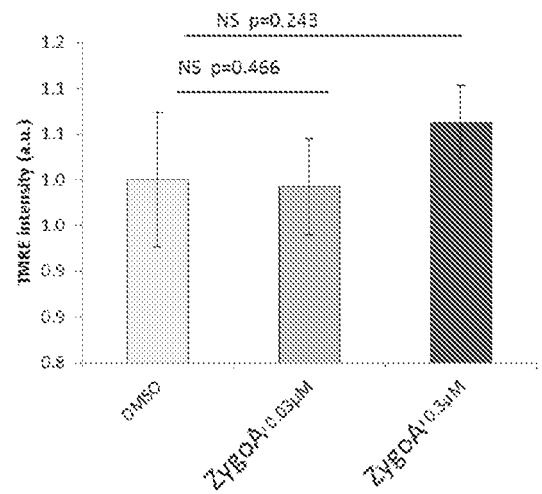
FIG. 12E is a graph showing that actin disruption did not change mitochondrial membrane potential (TMRE).
Figure 12F:
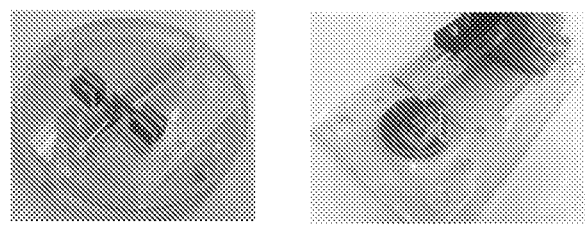
FIG. 12F are images showing that tissue level micro-tensile testing showed a decrease in axial stiffness at the same timescale as an increase in active contraction.

Tissue level micro-tensile testing showed a decrease in axial stiffness at the same timescale as an increase in active contraction (FIG. 12A-12C). F-actin stabilization by jasplakinolide lead to a gradual decrease in active contractility, showing that the opposite of F-actin disruption lead to the functionally opposite response of force improvement (FIG. 12D-12E). Actin disruption did not change mitochondrial enzymatic activity (MTT, FIG. 12D) or Mitochondrial membrane potential (TMRE, FIG. 12E).

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for increasing muscle strength, comprising contacting a skeletal or smooth muscle of a subject in need thereof with a pharmacological agent comprising an F-actin disrupting agent at a dosage between about 0.01 to about 20 mg per kg of the subject applied for less than or equal to 5 hours to transiently depolymerize actin thereby reducing mechanical stiffness of a muscle tissue, wherein the F-actin disrupting agent comprises an actin nuclease inhibitor or tropomyosin inhibitor.

2. The method of claim 1, wherein said actin nuclease inhibitor comprises SMIFH2 and wherein said tropomyosin inhibitor comprises ATM-3507.

3. The method of claim 1, wherein said skeletal or smooth muscle is diseased or functionally compromised.

4. The method of claim 1, wherein said subject comprises a muscle wasting disorder, a muscle degenerative disease, or exercise-induced muscle weakness.

5. The method of claim 1, wherein said muscle strength is increased by at least 10% compared to the level of muscle strength prior to said contacting step.

6. The method of claim 1, wherein an increase in muscle strength commences 0.1-5 hours post-administration.

7. The method of claim 1, wherein the pharmacological agent comprises the F-actin disrupting agent at a dosage between about 0.3 to about 5 mg per kg of the subject.

8. The method of claim 1, wherein the pharmacological agent comprising the F-actin disrupting agent is applied for about 2 hours.

9. A method for increasing muscle strength in a subject in need thereof, the method comprising:
    contacting a skeletal muscle of the subject with an F-actin disrupting agent at a dosage between about 0.01 to about 20 mg per kg of the subject applied for less than or equal to 5 hours thereby transiently depolymerizing actin, wherein the F-actin disrupting agent comprises an actin nuclease inhibitor or tropomyosin inhibitor.

10. The method of claim 9, wherein said skeletal muscle is diseased or functionally compromised, wherein said diseased or functionally compromised skeletal muscle is the result of a muscle wasting disorder, cancer, or exercise-induced muscle weakness.

11. The method of claim 10, wherein the muscle wasting disorder comprises amyotrophic lateral sclerosis (ALS), Duchenne Muscular Dystrophy (DMD), cachexia, sarcopenia, human immunodeficiency syndrome (HIV), diabetes mellitus, or sepsis.

12. The method of claim 9, wherein the skeletal muscle is healthy skeletal muscle.

13. The method of claim 9, wherein said muscle strength is increased by at least 10% compared to the level of muscle strength prior to said contacting step.

14. The method of claim 9, wherein an increase in muscle strength commences about 0.1-5 hours post-administration.

15. The method of claim 9, wherein an increase in muscle strength commences about 24 hours post-administration.

16. The method of claim 9, wherein the pharmacological agent comprises the F-actin disrupting agent at a dosage between about 0.3 to about 5 mg per kg of the subject.

17. The method of claim 9, wherein the pharmacological agent comprising the F-actin disrupting agent is applied for about 2 hours.

18. A method of treating a subject who has a muscle wasting disorder, cancer, or exercise-induced muscle weakness, the method comprising:
    administering a pharmaceutical composition comprising an F-actin disrupting agent at a dosage between about 0.01 to about 20 mg per kg of the subject applied for less than or equal to 5 hours to the subject thereby transiently depolymerizing actin, wherein the F-actin disrupting agent comprises an actin nuclease inhibitor or tropomyosin inhibitor.

19. The method of claim 18, wherein the muscle wasting disorder comprises ALS, DMD, cachexia, sarcopenia, human immunodeficiency syndrome (HIV), diabetes mellitus, or sepsis.

20. The method of claim 18, wherein the pharmacological agent comprises the F-actin disrupting agent at a dosage between about 0.3 to about 5 mg per kg of the subject.

21. The method of claim 18, wherein the pharmacological agent comprising the F-actin disrupting agent is applied for about 2 hours.

* * * * *

SEQUENCE LISTING

```
<160> NUMBER OF SEQ ID NOS: 2

<210> SEQ ID NO 1
<211> LENGTH: 375
<212> TYPE: PRT
<213> ORGANISM: Artificial Sequence
<220> FEATURE:
<223> OTHER INFORMATION: Synthetic human F-actin

<400> SEQUENCE: 1

Met Asp Asp Asp Ile Ala Ala Leu Val Val Asp Asn Gly Ser Gly Met
1               5                   10                  15

Cys Lys Ala Gly Phe Ala Gly Asp Asp Ala Pro Arg Ala Val Phe Pro
            20                  25                  30

Ser Ile Val Gly Arg Pro Arg His Gln Gly Val Met Val Gly Met Gly
        35                  40                  45

Gln Lys Asp Ser Tyr Val Gly Asp Glu Ala Gln Ser Lys Arg Gly Ile
    50                  55                  60

Leu Thr Leu Lys Tyr Pro Ile Glu His Gly Ile Val Thr Asn Trp Asp
65                  70                  75                  80

Asp Met Glu Lys Ile Trp His His Thr Phe Tyr Asn Glu Leu Arg Val
                85                  90                  95

Ala Pro Glu Glu His Pro Val Leu Leu Thr Glu Ala Pro Leu Asn Pro
            100                 105                 110

Lys Ala Asn Arg Glu Lys Met Thr Gln Ile Met Phe Glu Thr Phe Asn
        115                 120                 125

Thr Pro Ala Met Tyr Val Ala Ile Gln Ala Val Leu Ser Leu Tyr Ala
    130                 135                 140

Ser Gly Arg Thr Thr Gly Ile Val Met Asp Ser Gly Asp Gly Val Thr
145                 150                 155                 160

His Thr Val Pro Ile Tyr Glu Gly Tyr Ala Leu Pro His Ala Ile Leu
                165                 170                 175

Arg Leu Asp Leu Ala Gly Arg Asp Leu Thr Asp Tyr Leu Met Lys Ile
            180                 185                 190

Leu Thr Glu Arg Gly Tyr Ser Phe Thr Thr Thr Ala Glu Arg Glu Ile
        195                 200                 205

Val Arg Asp Ile Lys Glu Lys Leu Cys Tyr Val Ala Leu Asp Phe Glu
    210                 215                 220

Gln Glu Met Ala Thr Ala Ala Ser Ser Ser Ser Leu Glu Lys Ser Tyr
225                 230                 235                 240
```

```
Glu Leu Pro Asp Gly Gln Val Ile Thr Ile Gly Asn Glu Arg Phe Arg
                245                 250                 255
Cys Pro Glu Ala Leu Phe Gln Pro Ser Phe Leu Gly Met Glu Ser Cys
            260                 265                 270
Gly Ile His Glu Thr Thr Phe Asn Ser Ile Met Lys Cys Asp Val Asp
        275                 280                 285
Ile Arg Lys Asp Leu Tyr Ala Asn Thr Val Leu Ser Gly Gly Thr Thr
    290                 295                 300
Met Tyr Pro Gly Ile Ala Asp Arg Met Gln Lys Glu Ile Thr Ala Leu
305                 310                 315                 320
Ala Pro Ser Thr Met Lys Ile Lys Ile Ile Ala Pro Pro Glu Arg Lys
                325                 330                 335
Tyr Ser Val Trp Ile Gly Gly Ser Ile Leu Ala Ser Leu Ser Thr Phe
            340                 345                 350
Gln Gln Met Trp Ile Ser Lys Gln Glu Tyr Asp Glu Ser Gly Pro Ser
        355                 360                 365
Ile Val His Arg Lys Cys Phe
    370                 375

<210> SEQ ID NO 2
<211> LENGTH: 1940
<212> TYPE: DNA
<213> ORGANISM: Artificial Sequence
<220> FEATURE:
<223> OTHER INFORMATION: Synthetic Human F-Actin

<400> SEQUENCE: 2
gagtgagcgg cgcggggcca atcagcgtgc gccgttccga aagttgcctt ttatggctcg      60
agcggccgcg gcggcgccct ataaaaccca gcggcgcgac gcgccaccac cgccgagacc     120
gcgtccgccc cgcgagcaca gagcctcgcc tttgccgatc cgccgcccgt ccacacccgc     180
cgccagctca ccatggatga tgatatcgcc gcgctcgtcg tcgacaacgg ctccggcatg     240
tgcaaggccg gcttcgcggg cgacgatgcc ccccggggccg tcttcccctc catcgtgggg     300
cgccccaggc accagggcgt gatggtgggc atgggtcaga aggattccta tgtgggcgac     360
gaggcccaga gcaagagagg catcctcacc ctgaagtacc ccatcgagca cggcatcgtc     420
accaactggg acgacatgga gaaaatctgg caccacacct tctacaatga gctgcgtgtg     480
gctcccgagg agcaccccgt gctgctgacc gaggcccccc tgaaccccaa ggccaaccgc     540
gagaagatga cccagatcat gtttgagacc ttcaacaccc cagccatgta cgttgctatc     600
caggctgtgc tatccctgta cgcctctggc cgtaccactg gcatcgtgat ggactccggt     660 gacgggtca cccacactgt gcccatctac gaggggtatg ccctccccca tgccatcctg     720
cgtctggacc tggctggccg ggacctgact gactacctca tgaagatcct caccgagcgc     780
ggctacagct tcaccaccac ggccgagcgg gaaatcgtgc gtgacattaa ggagaagctg     840
tgctacgtcg ccctggactt cgagcaagag atggccacgg ctgcttccag ctcctccctg     900
gagaagagct acgagctgcc tgacggccag gtcatcacca ttggcaatga gcggttccgc     960
tgccctgagg cactcttcca gccttccttc ctgggcatgg agtcctgtgg catccacgaa    1020
actaccttca actccatcat gaagtgtgac gtggacatcc gcaaagacct gtacgccaac    1080
acagtgctgt ctggcggcac caccatgtac cctggcattg ccgacaggat gcagaaggag    1140
atcactgccc tggcacccag cacaatgaag atcaagatca ttgctcctcc tgagcgcaag    1200
tactccgtgt ggatcggcgg ctccatcctg gcctcgctgt ccaccttcca gcagatgtgg    1260
```

```
atcagcaagc aggagtatga cgagtccggc ccctccatcg tccaccgcaa atgcttctag    1320
gcggactatg acttagttgc gttacaccct ttcttgacaa aacctaactt gcgcagaaaa    1380
caagatgaga ttggcatggc tttatttgtt tttttttgttt tgttttggtt tttttttttt   1440
ttttggcttg actcaggatt taaaaactgg aacggtgaag gtgacagcag tcggttggag    1500
cgagcatccc ccaaagttca caatgtggcc gaggactttg attgcacatt gttgttttt    1560 taatagtcat tccaaatatg agatgcgttg ttacaggaag tcccttgcca tcctaaaagc    1620
caccccactt ctctctaagg agaatggccc agtcctctcc caagtccaca caggggaggt    1680
gatagcattg ctttcgtgta aattatgtaa tgcaaaattt ttttaatctt cgccttaata    1740
cttttttatt ttgttttatt ttgaatgatg agccttcgtg ccccccttc cccttttttt     1800 gtcccccaac ttgagatgta tgaaggcttt tggtctccct gggagtgggt ggaggcagcc    1860
agggcttacc tgtacactga cttgagacca gttgaataaa agtgcacacc ttaaaaatga    1920
ggaaaaaaaa aaaaaaaaaa                                                1940
```